US010969583B2

(12) United States Patent
Hresko et al.

(10) Patent No.: US 10,969,583 B2
(45) Date of Patent: Apr. 6, 2021

(54) AUGMENTED REALITY INFORMATION SYSTEM FOR USE WITH A MEDICAL DEVICE

(71) Applicant: ZOLL Medical Corporation, Chelmsford, MA (US)

(72) Inventors: Patrick Hresko, Mount Pleasant, PA (US); Thomas E. Kaib, Irwin, PA (US); Shane S. Volpe, Saltsburg, PA (US); Grace Owens, Pittsburgh, PA (US); Trisha A. Pavel, Pittsburgh, PA (US); John G. Clark, Pittsburgh, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 15/442,280

(22) Filed: Feb. 24, 2017

(65) Prior Publication Data
US 2018/0242920 A1 Aug. 30, 2018

(51) Int. Cl.
*G02B 27/01* (2006.01)
*A61B 5/0408* (2006.01)
(Continued)

(52) U.S. Cl.
CPC ........ *G02B 27/0172* (2013.01); *A61B 5/0006* (2013.01); *A61B 5/04085* (2013.01);
(Continued)

(58) Field of Classification Search
CPC . G06T 7/00; G06T 11/00; G06T 13/20; G06T 19/00; G06T 19/006;
(Continued)

(56) References Cited

U.S. PATENT DOCUMENTS 9,277,248 B1 * 3/2016 Levy ...................... H04N 21/00
9,734,295 B1 * 8/2017 Movva .................. A61B 5/1116
(Continued)

OTHER PUBLICATIONS

Silva et al. (2004). Applying Object Recognition and Tracking to Augmented Reality for Information Visualization, pp. 1-7.

*Primary Examiner* — Sae Won Yoon
(74) *Attorney, Agent, or Firm* — Finch & Maloney PLLC

(57) ABSTRACT

An augmented-reality system for providing information relating to a wearable medical device and/or a patient wearing a medical device. An augmented-reality enabled computing device includes an image acquisition device, a user interface operatively coupled to the image acquisition device, the user interface configured to receive streaming images of a scene having one or more predetermined recognizable features, and a processor operably connected to the user interface. The processor is configured receive the streaming images, analyze the one or more predetermined recognizable features to determine a context of the scene, retrieve information relating to at least one of the medical device and the patient wearing the medical device, the information corresponding to the determined context of the scene, and augment the received streaming images with contextual information relating to at least one of the medical device and the patient wearing the medical device.

26 Claims, 12 Drawing Sheets

(51) Int. Cl.
| | |
|---|---|
| *A61M 1/04* | (2006.01) |
| *A61B 5/00* | (2006.01) |
| *G06K 9/00* | (2006.01) |
| *A61N 1/39* | (2006.01) |
| *A61N 1/36* | (2006.01) |
| *G06F 3/01* | (2006.01) |
| *A61B 90/96* | (2016.01) |
| *A61B 5/1171* | (2016.01) |
| *A61B 5/11* | (2006.01) |
| *A61B 5/145* | (2006.01) |
| *A61B 5/021* | (2006.01) |
| *A61B 5/0205* | (2006.01) |
| *A61N 1/04* | (2006.01) |

(52) U.S. Cl.
CPC ............ *A61B 5/6804* (2013.01); *A61B 5/743* (2013.01); *A61N 1/0484* (2013.01); *A61N 1/36014* (2013.01); *A61N 1/3904* (2017.08); *G06F 3/011* (2013.01); *G06K 9/00671* (2013.01); *G06K 9/00718* (2013.01); *A61B 5/021* (2013.01); *A61B 5/02055* (2013.01); *A61B 5/1118* (2013.01); *A61B 5/1176* (2013.01); *A61B 5/14532* (2013.01); *A61B 5/14542* (2013.01); *A61B 5/7405* (2013.01); *A61B 5/7455* (2013.01); *A61B 5/7475* (2013.01); *A61B 90/96* (2016.02); *G02B 27/017* (2013.01); *G02B 2027/014* (2013.01); *G02B 2027/0138* (2013.01); *G02B 2027/0141* (2013.01); *G02B 2027/0178* (2013.01)

(58) Field of Classification Search
CPC ...... G06T 2210/41; G06F 19/30; G06F 3/011; G06F 19/3487; H04N 13/0488; A61B 5/0006; A61B 5/02055; A61B 5/021; A61B 5/04085; A61B 5/1118; A61B 5/1176; A61B 5/14532; A61B 5/14542; A61B 5/6804; A61B 5/7405; A61B 5/743; A61B 5/7455; A61B 5/7475; A61B 90/96; A61N 1/3904; A61N 1/36014; A61N 1/0484; G02B 27/017; G02B 27/0172; G02B 2027/0138; G02B 2027/014; G02B 2027/0141; G02B 2027/0178; G06K 9/00671; G06K 9/00718

USPC ........................................................ 345/633
See application file for complete search history.

(56) References Cited

U.S. PATENT DOCUMENTS

| | | | | |
|---|---|---|---|---|
| 9,852,599 | B1* | 12/2017 | Slavin | G08B 21/043 |
| 2005/0206654 | A1* | 9/2005 | Vaha-Sipila | G01C 21/20 345/632 |
| 2010/0298899 | A1* | 11/2010 | Donnelly | A61N 1/37258 607/6 |
| 2012/0329432 | A1* | 12/2012 | Gupta | G06Q 30/02 455/414.1 |
| 2014/0063053 | A1* | 3/2014 | Jung | H04M 1/274508 345/629 |
| 2014/0139405 | A1* | 5/2014 | Ribble | G06F 19/327 345/8 |
| 2014/0285520 | A1* | 9/2014 | Park | G06T 19/006 345/633 |
| 2014/0342331 | A1* | 11/2014 | Freeman | G09B 23/288 434/265 |
| 2015/0005588 | A1 | 1/2015 | Herken et al. | |
| 2015/0156196 | A1* | 6/2015 | Kim | G06F 21/32 345/156 |
| 2015/0187138 | A1* | 7/2015 | Mullins | G06T 19/006 345/633 |
| 2015/0205931 | A1* | 7/2015 | Wang | G16H 40/63 702/19 |
| 2015/0279117 | A1* | 10/2015 | Schimke | G06F 16/00 345/633 |
| 2016/0004831 | A1* | 1/2016 | Carlson | G06F 19/3406 705/2 |
| 2016/0022375 | A1* | 1/2016 | Blake | A61B 5/746 600/424 |
| 2016/0034042 | A1* | 2/2016 | Joo | G06T 19/006 345/633 |
| 2016/0041048 | A1* | 2/2016 | Blum | G01L 1/2206 73/774 |
| 2016/0178906 | A1* | 6/2016 | Rider | G02B 27/0172 726/17 |
| 2017/0039423 | A1* | 2/2017 | Cork | G02B 27/0176 |
| 2017/0039774 | A1* | 2/2017 | Estable | G02B 27/017 |
| 2017/0056682 | A1* | 3/2017 | Kumar | A61N 1/3968 |
| 2017/0112439 | A1* | 4/2017 | Dubin | A61B 7/04 |
| 2017/0186157 | A1* | 6/2017 | Boettger | G06T 7/50 |
| 2017/0273616 | A1* | 9/2017 | Yang | A61B 5/486 |
| 2017/0293923 | A1* | 10/2017 | Margolis | G06Q 30/0204 |
| 2018/0190382 | A1* | 7/2018 | Ramezani | H04L 67/22 |
| 2018/0322943 | A1* | 11/2018 | Johnson | G16H 50/70 |

* cited by examiner

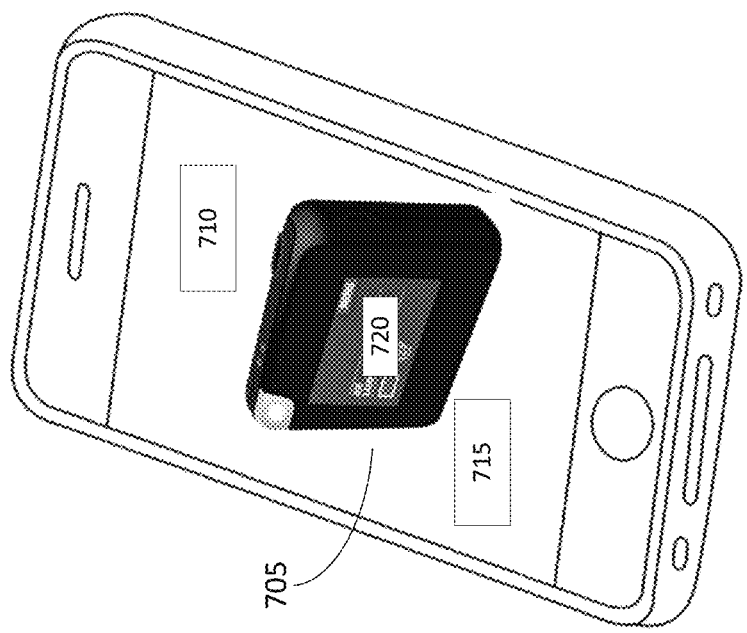
FIG. 7

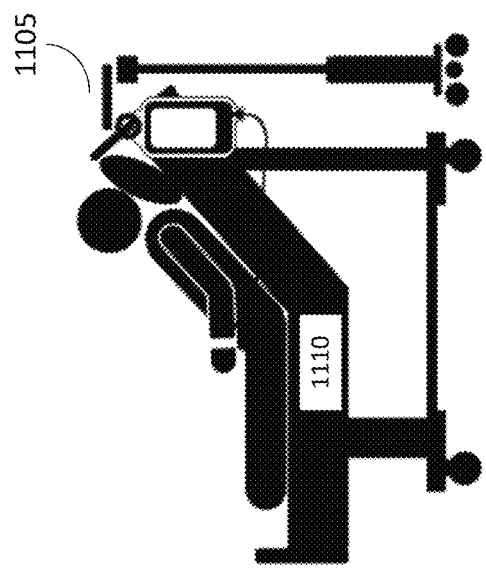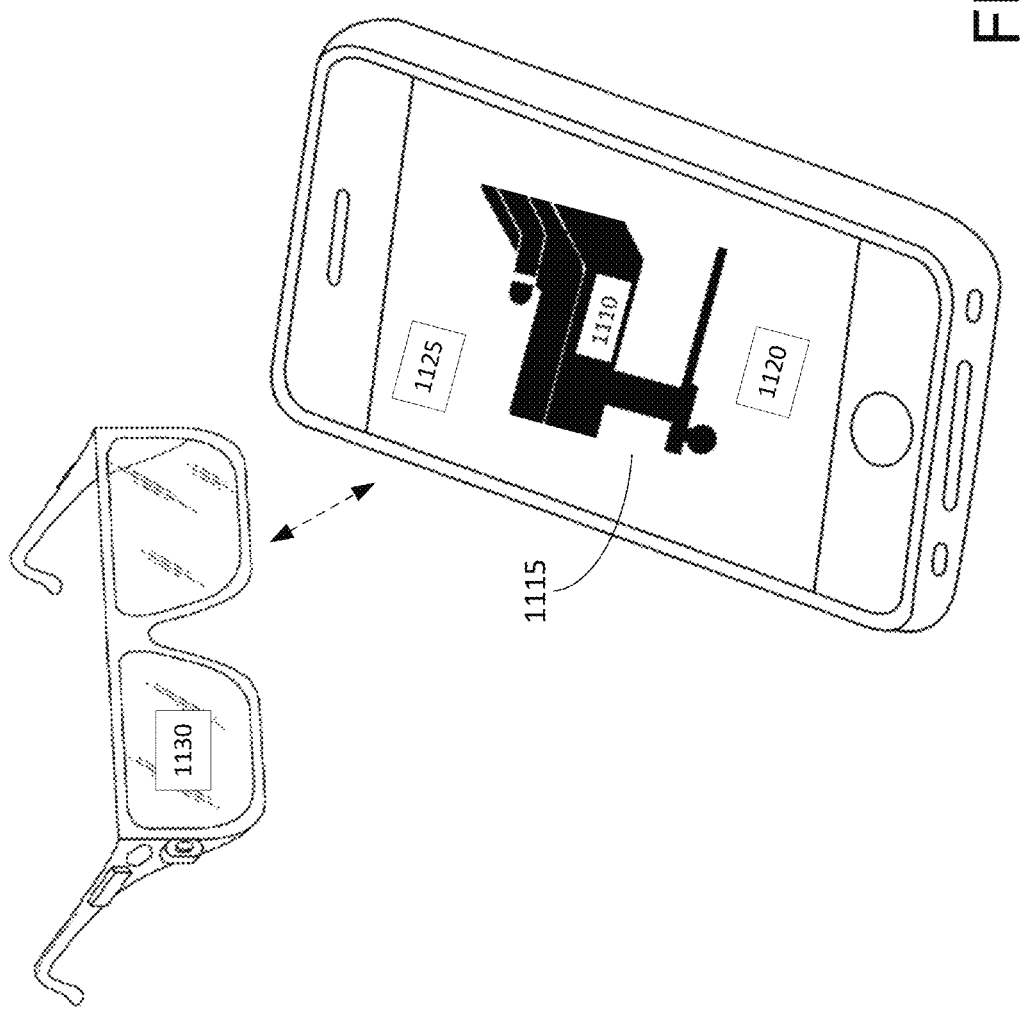
FIG. 11A

AUGMENTED REALITY INFORMATION SYSTEM FOR USE WITH A MEDICAL DEVICE

BACKGROUND

The present disclosure is directed to providing information related to a medical device, and more particularly, to providing information using an augmented or virtual reality device.

To protect against various health conditions such as cardiac arrest and other cardiac health ailments, some at-risk patients can wear a prescribed medical device for an extended period of time. For example, for patients at risk for cardiac events, they can be prescribed a non-invasive bodily-attached ambulatory medical monitoring and treatment device, such as the LifeVest® wearable cardioverter defibrillator available from ZOLL Medical Corporation. To remain protected, the patient wears the device nearly continuously while going about their normal daily activities, while awake, and while asleep.

When worn, the medical monitoring and treatment device can continually monitor one or more of the patient's physiological signals, recording information related to the monitored signals. Based upon detected or measured changes in the patient's physiological signal(s), the medical monitoring and treatment device can take one or more actions such as providing an alarm or a treatment to the patient. For example, for a wearable cardioverter defibrillator, the treatment can include a therapeutic shock.

However, many of the functions of the wearable medical devices can be confusing to a patient, even simple functions such as properly putting on the wearable medical device, and there may be no intuitive way for a patient to access support information related to the wearable medical device in a simple and timely manner.

SUMMARY

An augmented-reality system for providing information relating to a wearable medical device to a patient is described herein. The system includes an augmented-reality enabled computing device. In certain implementations, the augmented-reality enabled computing device includes an image acquisition device, a user interface operatively coupled to the image acquisition device, the user interface configured to receive streaming images of a scene having one or more predetermined recognizable features, and a processor operably connected to the user interface. In some examples, the processor is configured to execute one or more computer-readable instructions to cause the processor to receive the streaming images of the scene, process the streaming images to analyze the one or more predetermined recognizable features to determine a context of the scene, retrieve information relating to at least one of the wearable medical device and a patient wearing the wearable medical device, the information corresponding to the determined context of the scene, and based on the retrieved information relating to the wearable medical device, augment the received streaming images with contextual information relating to at least one of the wearable medical device and the patient wearing the wearable medical device.

In certain implementations of the above system, the one or more predetermined recognizable features includes an outline of at least a portion of the patient's body.

In certain implementations of the above system, processing the streaming images to analyze the one or more predetermined recognizable features to determine the context of the scene includes scanning the streaming images for a shape having one or more identified distinguishing features, comparing the one or more identified distinguishing features against a library of the predetermined recognizable features; identifying a match between the one or more identified distinguishing features and at least predetermined recognizable feature, and identifying the wearable medical device based upon the match. In some examples, the one or more identified distinguishing features includes at least one of a barcode, a serial number, a QR code, and an identified physical shape of at least one component of the wearable medical device.

In certain implementations of the above system, determining the context of the scene includes determining one or more components of the wearable medical device based upon the predetermined recognizable features. In some examples, the one or more components of the wearable medical device includes at least one of a wearable medical device monitor, a battery, a garment, an electrode belt, a sensing electrode, and a therapy electrode. In some examples, the contextual information includes diagnostic component information for the identified one or more components.

In certain implementations of the above system, the contextual information includes operating instructions for the wearable medical device. In some examples, the operating instructions comprise assembly instructions for assembling the wearable medical device.

In certain implementations of the above system, the contextual information includes instructions for a user of the computing device to orient the computing device such that the image acquisition device is directed to a specific component of the wearable medical device. In some examples, the processing device is further configured to retrieve component information related to the specific component of the wearable medical device, and augment the received streaming images with the component information.

In certain implementations of the above system, the computing device includes a personal computing device used by the patient wearing the wearable medical device. In some examples, the personal computing device includes a wearable computing device configured to provide at least one of audio, video and haptic feedback to a patient via the user interface.

In certain implementations of the above system, the computing device is configured to provide, via the user interface, an interactive experience simulating operation of the wearable medical device. In some examples, the interactive experience includes simulating a fibrillation and treatment event.

In certain implementations of the above system, the processing device is further configured to establish a communication session with a remote communications device, receive device information from the remote communication device, and augment the received streaming images with the device information. In some examples, the device information includes troubleshooting information related to the operation of the wearable medical device. In some further examples, the troubleshooting information includes a set of instructions for the user of the wearable medical device to perform.

In certain implementations of the above system, the contextual information includes activity information related to a task the patient is performing. In some examples, the task the patient is performing includes a walk test. In some further examples, the processor is further configured to execute one or more computer-readable instructions to cause the processor to query the patient wearing the wearable medical device to answer one or more questions upon completion of the walk test.

A second augmented-reality system for providing information relating to a wearable medical device to a caregiver of a patient is also described herein. The second system includes an augmented-reality enabled computing device. In certain implementations, the augmented-reality enabled computing device includes an image acquisition device, a user interface operably coupled to the image acquisition device, the user interface configured to receive streaming images of at least one of a wearable medical device and a patient wearing the wearable medical device, the streaming images including one or more predetermined recognizable features, and a processor operably connected to the user interface. The processor is configured to execute one or more computer-readable instruction to cause the processor to receive the streaming images of the wearable medical device, process the streaming images to analyze the one or more predetermined recognizable features to determine at least one of the wearable medical device and the patient wearing the wearable medical device, retrieve additional information relating to at least one of the wearable medical device and the patient wearing the wearable medical device, and augment the received streaming images with the retrieved additional information.

In certain implementations of the above second system, the retrieved additional information includes at least one of patient physiological information and operational information for the wearable medical device. In some examples, augmenting the received streaming images with the retrieved additional information includes displaying the patient physiological information on the augmented-reality enabled computing device.

In certain implementations of the above second system, processing the streaming images to analyze the one or more predetermined recognizable features to determine the context of the scene includes scanning the streaming images for a shape having one or more identified distinguishing features, comparing the one or more identified distinguishing features against a library of the predetermined recognizable features, identifying a match between the one or more identified distinguishing features and at least predetermined recognizable feature, and identifying at least one of the wearable medical device and the patient wearing the wearable medical device based upon the match. In some examples, the one or more identified distinguishing features includes at least one of a barcode, a serial number, a QR code, and an identified physical shape of at least one component of the wearable medical device. In some additional examples, the one or more predetermined recognizable features includes an outline of at least a portion of the patient's body and, in some implementations, comparing the one or more identified distinguishing features against a library of the predetermined recognizable features includes performing a facial recognition process.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended as a definition of the limits of any particular example. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

FIG. 7 depicts a sample view of operational information related to a wearable medical device augmented onto the patient's computing device, in accordance with an example of the present disclosure.

FIGS. 11A and 11B illustrate sample views of additional information related to a patient as displayed on a caregiver's computing device, in accordance with an example of the present disclosure.

DETAILED DESCRIPTION

Figure 1:
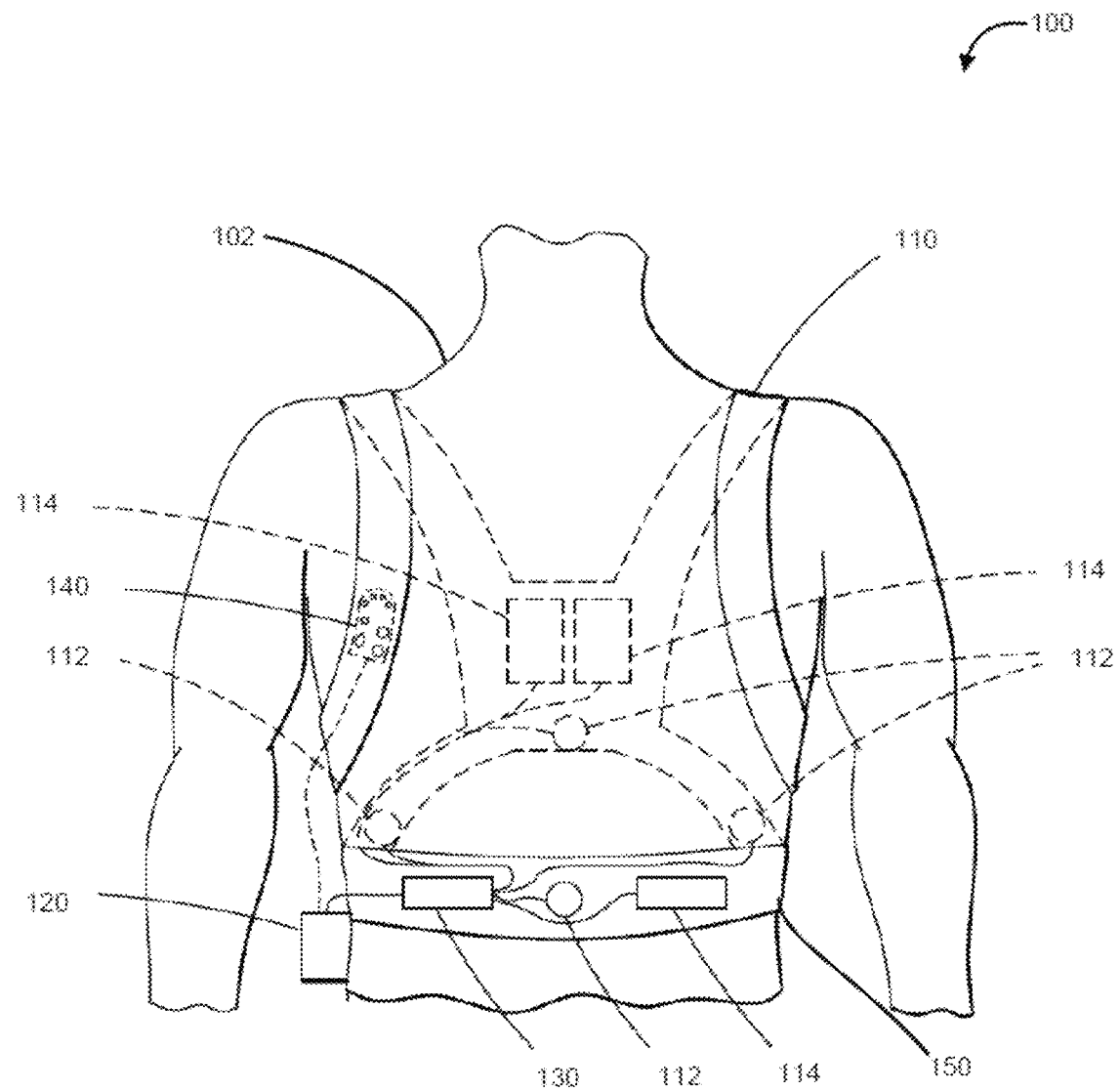
FIG. 1 depicts a wearable medical device, in accordance with an example of the present disclosure.

As used herein, the singular form of "a", "an", and "the" include plural referents unless the context clearly dictates otherwise. Similarly, as used herein, the terms "end", "upper", "lower", "right", "left", "vertical", "horizontal", "top", "bottom", "lateral", "longitudinal" and derivatives thereof shall relate to the invention as it is oriented in the drawing figures. However, it is to be understood that the invention can assume various alternative orientations and, accordingly, such terms are not to be considered as limiting. Also, it is to be understood that the invention may assume various alternative variations and stage sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

For the purposes of this specification, unless otherwise indicated, all numbers expressing quantities of ingredients, reaction conditions, dimensions, physical characteristics, and so forth used in the specification and claims are to be understood as being modified in all instances by the term "about." Accordingly, unless indicated to the contrary, the numerical parameters set forth in the following specification and attached claims are approximations that can vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include any and all sub-ranges between and including the recited minimum value of 1 and the recited maximum value of 10, that is, all subranges beginning with a minimum value equal to or greater than 1 and ending with a maximum value equal to or less than 10, and all subranges in between, e.g., 1 to 6.3, or 5.5 to 10, or 2.7 to 6.1.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that can be wired and/or wireless in nature. Additionally, two units or components can be in communication with each other even though the data transmitted can be modified, processed, routed, and the like, between the first and second unit or component. For example, a first unit can be in communication with a second unit even though the first unit passively receives data, and does not actively transmit data to the second unit. As another example, a first unit can be in communication with a second unit if an intermediary unit processes data from one unit and transmits processed data to the second unit. It will be appreciated that numerous other arrangements are possible.

This disclosure relates to providing augmented reality capabilities to a user's personal device to provide information related to a medical device or a patient using a medical device. For example, a patient that has been prescribed a wearable medical device such as the LifeVest® wearable cardioverter defibrillator available from ZOLL® Medical Corporation can also be given access to an application or portable medical device that is configured to provide the patient with additional contextual information related to their use of the wearable medical device. In certain implementations, the patient can access the application on a portable computing device such as a smartphone or tablet computing device. The application can be configured to receive a set of streaming images from an image acquisition device integrated into the portable computing device. The application can process the received streaming images to determine if one or more predetermined recognizable features are present in the streaming images. If the application determines that there are one or more predetermined recognizable features in the streaming images, the application can retrieve additional contextual information relating to the wearable medical device and augment the streaming images with the contextual information for display on the portable computing device.

Additionally, the application can provide a gateway or portal for accessing technical support related to operation of the medical device. For example, a technical support specialist can also access the streaming images to identify what the patient is looking at (e.g., the medical device) and attempt to troubleshoot or identify any problems associated with the medical device. The technical support specialist can then augment the streaming images with additional information specific to that medical device for display on the portable computing device (associated with the patient) such that the patient receives the specific information.

Such augmented reality capabilities can be extended beyond merely a patient using the medical device. For example, a caregiver associated with the patient can have a similar portable computing device (e.g., a wearable computing device such as an augmented reality headset) for receiving information related to both a medical device as well as a patient associated with the medical device. For example, a caregiver application can be configured to process a set of streaming images to determine one or more predetermined recognizable features in the images to determine both the medical device as well as a patient using the medical device. For example, there can be a QR code, barcode, or other similar symbol associated with the medical device that can be included in the streaming images. The application can then retrieve information specific to that medical device and/or patient and augment the streaming images such that the information is provided to the caregiver. For example, in a hospital setting, a nurse can have an augmented reality headset. The nurse can enter a patient's room, look at their medical device (or another similar feature that would be recognizable to the caregiver application), and the caregiver application can identify the medical device, the associated patient, and access current physiological data related to the patient for display to the nurse.

Additionally, the application can be configured to identify a patient. For example, the application can include facial recognition software configured to identify a patient that the caregiver is looking at. In some implementations, the patient can wear a wristband or other similar article that includes some identification information such as a QR code, barcode, or other similar symbol that the application can use to identify the patient.

Example Wearable Therapeutic Device

FIG. 1 illustrates an example medical device 100 that is external, ambulatory, and wearable by a patient 102, and configured to implement one or more configurations described herein. For example, the medical device 100 can be a non-invasive medical device configured to be located substantially external to the patient. Such a device can be, for example, an ambulatory medical device that is capable of and designed for moving with the patient as the patient goes about his or her daily routine. For example, the medical device 100 as described herein can be bodily-attached to the patient such as the LifeVest® wearable cardioverter defibrillator available from ZOLL® Medical Corporation. Such wearable defibrillators typically are worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic electrical pulses to the patient. For example, such therapeutic shocks can be pacing, defibrillation, or transcutaneous electrical nerve stimulation (TENS) pulses.

The medical device 100 can include one or more of the following: a garment 110, one or more sensing electrodes 112 (e.g., ECG electrodes), one or more therapy electrodes 114, a medical device controller 120, a connection pod 130, a patient interface pod 140, a belt 150, or any combination of these. In some examples, at least some of the components of the wearable medical device 100 can be configured to be affixed to the garment 110 (or in some examples, permanently integrated into the garment 110), which can be worn about the patient's torso.

The controller 120 can be operatively coupled to the sensing electrodes 112, which can be affixed to the garment 110, e.g., assembled into the garment 110 or removably attached to the garment, e.g., using hook and loop fasteners. In some implementations, the sensing electrodes 112 can be permanently integrated into the garment 110. The controller 120 can be operatively coupled to the therapy electrodes 114. For example, the therapy electrodes 114 can also be assembled into the garment 110, or, in some implementations, the therapy electrodes 114 can be permanently integrated into the garment 110. Additionally, the therapy electrodes 114 can include one or more conductive gel deployment devices such as the devices described herein and, as other examples, devices described in U.S. Patent Application Publication No. 2012/0150164 entitled "Therapeutic Device Including Acoustic Sensor," the content of which is incorporate herein by reference.

Component configurations other than those shown in FIG. 1 are possible. For example, the sensing electrodes 112 can be configured to be attached at various positions about the body of the patient 102. The sensing electrodes 112 can be operatively coupled to the medical device controller 120 through the connection pod 130. In some implementations, the sensing electrodes 112 can be adhesively attached to the patient 102. In some implementations, the sensing electrodes 112 and therapy electrodes 114 can be included on a single integrated patch and adhesively applied to the patient's body.

The sensing electrodes 112 can be configured to detect one or more cardiac signals. Examples of such signals include ECG signals, heart sounds, and/or other sensed cardiac physiological signals from the patient. The sensing electrodes 112 can also be configured to detect other types of patient physiological parameters, such as tissue fluid levels, lung sounds, respiration sounds, patient movement, etc. In some examples, the therapy electrodes 114 can also be configured to include sensors configured to detect ECG signals as well as other physiological signals of the patient. The connection pod 130 can, in some examples, include a signal processor configured to amplify, filter, and digitize these cardiac signals prior to transmitting the cardiac signals to the controller 120. One or more therapy electrodes 114 can be configured to deliver one or more therapeutic defibrillating shocks to the body of the patient 102 when the medical device 100 determines that such treatment is warranted based on the signals detected by the sensing electrodes 112 and processed by the controller 120.

In some implementations, the wearable medical device can be a non-therapeutic patient monitoring device for an ambulatory patient, such as cardiac event monitoring (CEM) device or mobile cardiac telemetry (MCT) device. CEM devices collect cardiac information, such as a patient electrocardiogram (ECG) data, and provide the information to an external network or remote server on a periodic basis. Mobile cardiac telemetry (MCT) devices monitor patient physiological information, such as ECG, and send data aperiodically, such as when a particular triggering event is identified. MCT devices can further comprise additional sensors for measuring non-ECG physiological parameters. Data from non-ECG sensors can be provided along with ECG recordings for identified events.

CEM and MCT devices can be used for monitoring patient cardiac function for a predetermined interval (e.g., a number of days or weeks) to provide information about frequency and duration of cardiac events experienced by a patient. Cardiac events that can be identified by patient monitors can include, without limitation, one or more of atrial fibrillation, bradycardia, tachycardia, atrio-ventricular block, Lown-Ganong-Levine syndrome, atrial flutter, sino-atrial node dysfunction, cerebral ischemia, syncope, atrial pause, and/or heart palpitations. The collected information about identified cardiac events can be used, for example, to produce patient reports for time periods of interest.

A patient monitor (e.g., an MCT device) can include a controller, similar to the controller 120 as shown in FIG. 1, though without operably connected therapeutic components such as, for example, therapy electrodes 114 as shown in FIG. 1. The patient monitor controller can be communicatively coupled (e.g., wired or wirelessly coupled) to sensors and/or electrodes appropriately positioned on patient to obtain signals (e.g., ECG data and/or heart sounds data from an acoustic sensor) indicative of cardiac activity. In some examples, the patient monitor controller can, in addition to cardiac monitoring, perform monitoring of other relevant patient parameters, e.g., weight, glucose levels, blood oxygen levels, and blood pressure. The patient monitor controller can also comprise motion sensors to track patient movement. In some examples, the patient monitor can be in the form of an application on a handheld device, such as a smartphone, a personal digital assistant, or a tablet device.

The patient monitor can also include a physiological data processing component for collecting and conditioning the physiological data prior to storing the data locally at computer-readable storage media on the monitor itself and/or transmitting the data to a remote server or device. In some examples, the patient monitor controller can further include a user interface module that allows the patient to manually enter information about a patient condition, and to initiate sending information to the remote server.

Sample Mobile Device

Figure 2:
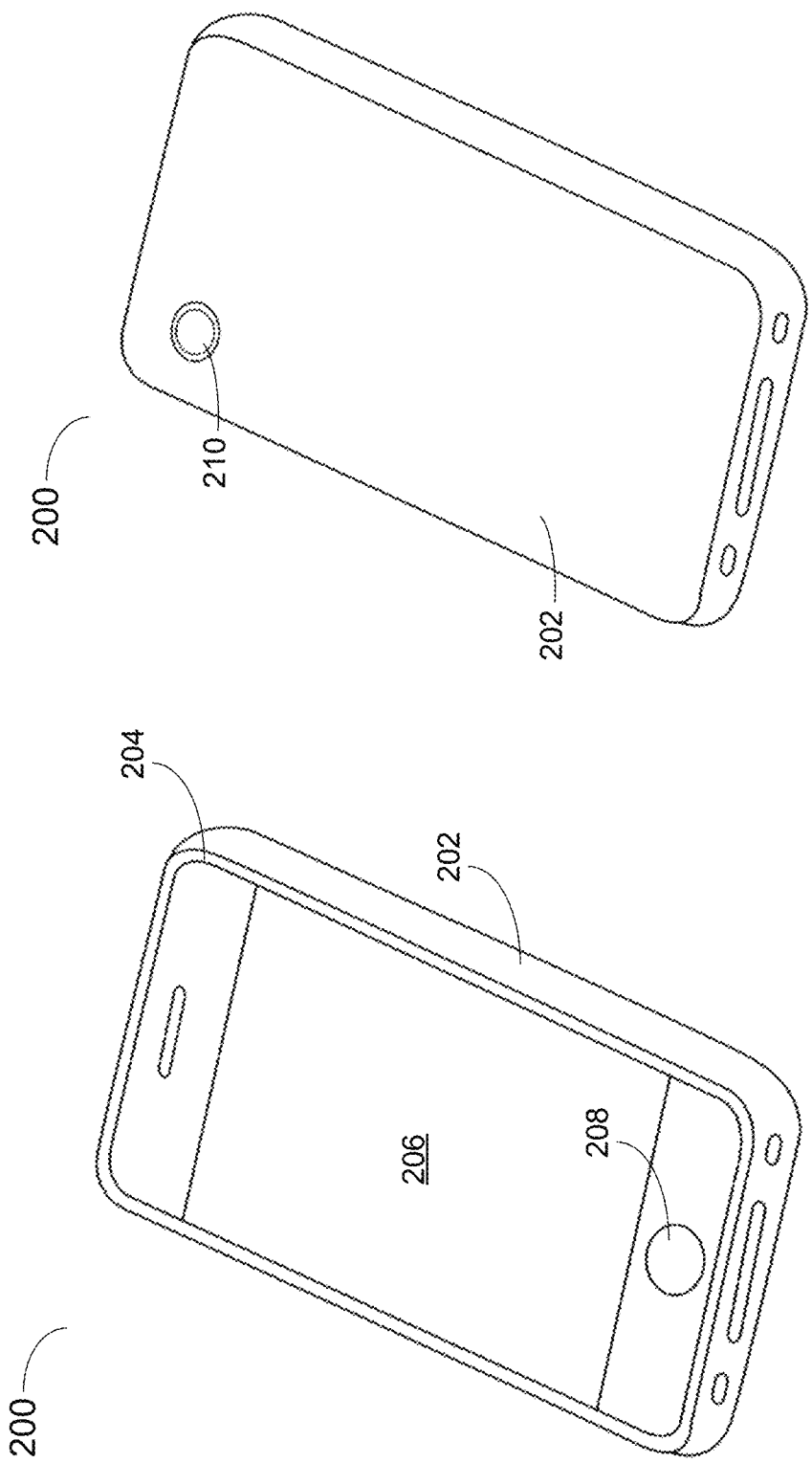
FIGS. 2A and 2B depict sample views of a portable computing device, in accordance with an example of the present disclosure.
Figure 3:
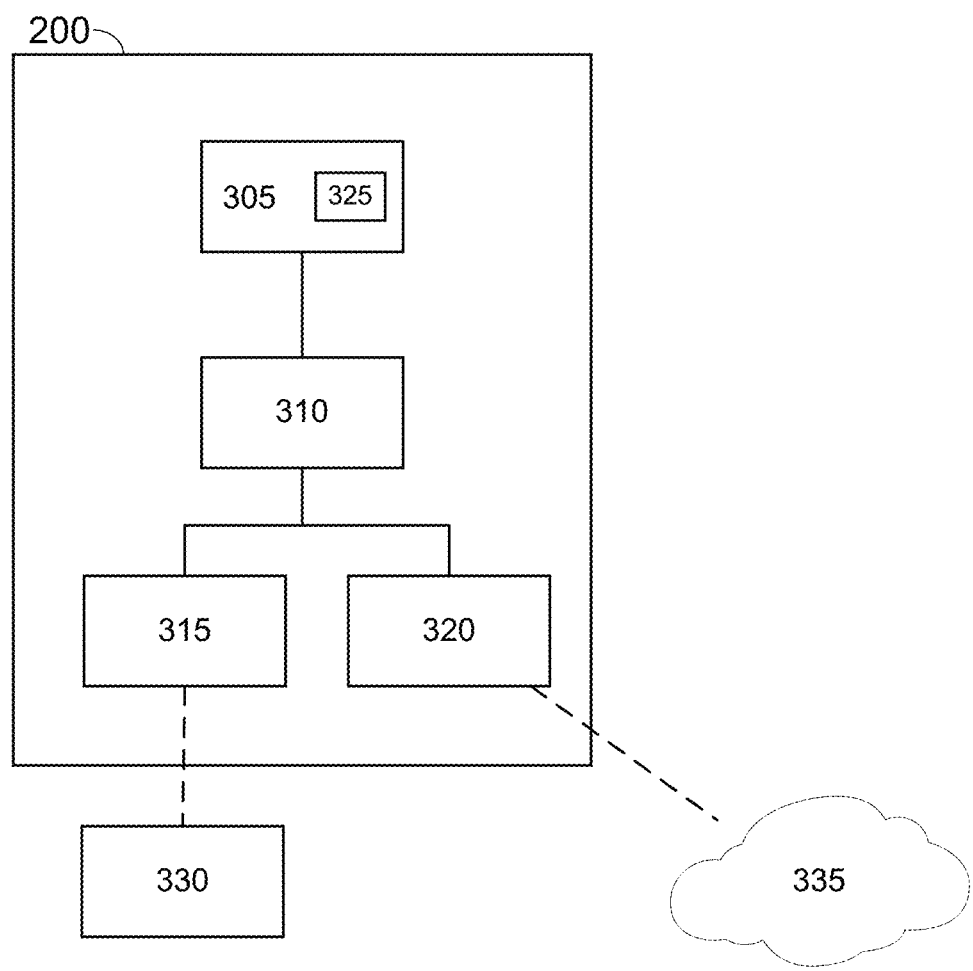
FIG. 3 depicts a sample architecture for a portable computing device such as that illustrated in FIGS. 2A and 2B, in accordance with an example of the present disclosure.

FIGS. 2A, 2B, and 3 illustrate various views of a mobile device. FIG. 2A illustrates an exterior front view of a sample mobile device 200 that can be configured to operably connect to one or more communication networks. Similarly, FIG. 2B illustrates a rear view of device 200. FIGS. 2A and 2B will be described herein simultaneously. The device 200 may be, for example, a cellular telephone, a media player with wireless communications capabilities, or a hybrid device (commonly referred to as a "smartphone") that combines several functions, including wireless telephony, web browsing, digital media player, and global positioning system, into the same handset unit. Examples of hybrid portable electronic devices include a cellular telephone that includes media player functionality, a gaming device that includes a wireless communications capability, a cellular telephone that includes game and email functions, and a portable device that receives email, supports mobile telephone calls, has music player functionality and supports web browsing.

The device 200 can include a housing 202. The housing 202 can be formed of any suitable materials including, plastic, glass, ceramics, metal, or other suitable materials, or a combination of these materials. In some situations, the entire housing 202 or portions of the housing 202 can be formed from a dielectric or other low-conductivity material, so that the operation of conductive antenna elements of the device 200 that are located within or in proximity to housing 202 is not disrupted. Housing 202 or portions of housing 202 can also be formed from conductive materials such as metal. For example, the housing 202 can be formed from anodized aluminum. Aluminum is relatively light in weight and, when anodized, provides insulation as well as a scratch-resistant surface. It should be noted that other metals can be used for the housing 202, such as stainless steel, magnesium, titanium, alloys of these metals and other metals.

Depending upon the design, the housing 202 can include a bezel 204. The bezel 204 can be formed from a similar material as the housing 202 and be configured to hold a display or other device with a planar surface in place on device 200. As shown in FIG. 2, for example, bezel 204 can be used to hold display 206 in place.

The display 206 can be a liquid crystal diode (LCD) display, an organic light emitting diode (OLED) display, or any other suitable display. The outermost surface of display 206 can be formed from one or more plastic or glass layers. In certain implementations, touch screen functionality can be integrated into display 206, or can be provided using a separate touch pad device, thus providing an interactive user interface. It should be noted that display 206 (e.g., a touch screen) is merely one example of an input-output device that may be used with device 200. If desired, electronic device 200 may have other input-output devices such as a home or menu button 208. In certain implementations, device 200 can have additional user input control devices such as alphanumeric keys, power on-off, power-on, power-off, volume control buttons, other specialized buttons, a touch pad, pointing stick, or other cursor control device, a microphone for supplying voice commands, or any other suitable interface for controlling device 200.

The device 200 can also include one or more image acquisition devices such as camera 210. One or more cameras 210 can be integrated into the housing 202 of the device 200. For example, as shown in FIG. 2B, a rear-facing camera 210 can be integrated into device 200. However, it should be noted that this is shown by way of example. Additional image acquisition devices such as a forward-facing camera can be integrated into the device 200 as well.

FIG. 3 illustrates a sample internal schematic for a mobile device such as device 200. As shown in FIG. 3, device 200 may include memory 305. Memory 305 can include one or more different types of non-transitory computer readable media such as hard disk drive storage, nonvolatile memory (e.g., flash memory or other electrically-programmable-read-only memory), volatile memory (e.g., battery-based static or dynamic random-access-memory), and other types of computer readable media.

The device 200 can also include a processor 310 operably connected to the memory 305 and configured to control the operation of device 200. The processor 310 can be configured to run one or more applications 325 stored on memory 305, thereby causing device 200 to perform one or more functions. For example, the processor 310 can be configured to run applications such as interact browsing applications, voice-over-internet-protocol (VOIP) telephone call applications, email applications, media playback applications, operating system functions, and other similar functionality.

The processor can be operably connected to an input/output interface controller 315. For example, the input/output controller 315 can be configured to provide an operable connection between the processor 310 and a user input device such as screen 206 as shown in FIG. 2A. In certain implementations, input/output controller 315 can be configured to attach to one or more accessory devices 330. For example, the input/output controller 315 can be configured to connect to headphones, an external keypad or keyboard, a microphone, and other similar accessories.

The processor 310 can also be operably connected to a communications interface 320. The communications interface 320 can be configured to establish a connection to a communications network 335. For example, the communications interface 320 can be configured to establish a connection to a cellular data network and configured to implement suitable communications protocols. For example, the communications can include internet protocols, wireless local area network protocols (e.g., IEEE 802.11 protocols commonly referred to as Wi-Fi), protocols for other short-range wireless communications links such as the Bluetooth® protocol, protocols for handling 4G communications services (e.g., using wide band code division multiple access techniques), 3G communication protocols, 2G cellular telephone communications protocols, near-field communication protocols, and other similar communication protocols.

The communications interface 320 can include communications circuitry such as radio-frequency (RF) transceiver circuitry formed from one or more integrated circuits, power amplifier circuitry, passive RF components, antennas, and other circuitry for handling RF wireless signals. Wireless signals can also be sent using light (e.g., using infrared communication protocols).

Sample Wearable Device

Figure 4:
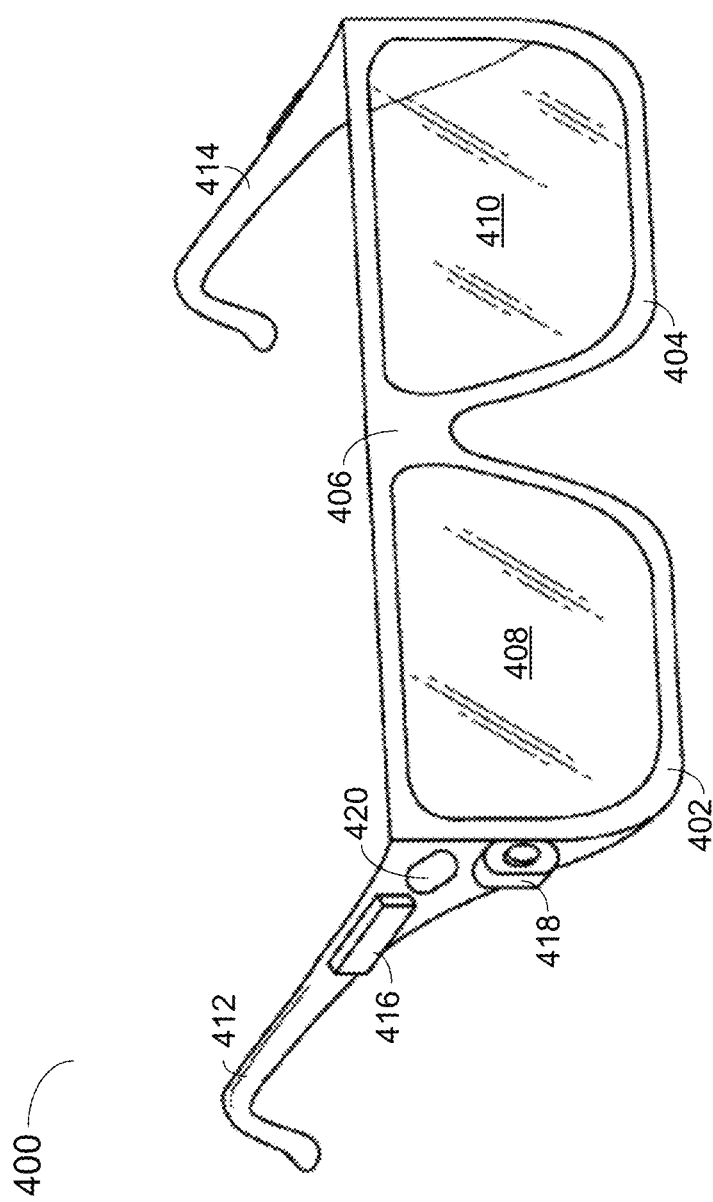
FIG. 4 depicts a sample wearable computing device, in accordance with an example of the present disclosure.

FIG. 4 illustrates an example wearable computing device 400 configured to receive, transmit, and display data. It should be noted that wearable computing device 400 is shown as a pair of glasses by way of example only. Additional wearable devices such as a full headset (including, for example, a portion configured to cover some or all of a wearer's head) can be included when considering the techniques and teachings described herein. Examples of wearable computing device include, but are not limited to, Google Glass™, Microsoft HoloLens™, Sony SmartEyeglass™, Vuzix M3000 AR glasses, Oculus Rift™, HTC Vive™, Samsung Gear VR™, and other similar wearable computing devices configured to provide an augmented reality or virtual reality experience to the wearer.

As illustrated in FIG. 4, the wearable computing device 400 can include various structural elements such as lens-frames 402, 404, and a center frame support 406, lens elements 408, 410, and extending side-arms 412, 414. The center frame support 406 and the extending side-arms 412, 414 can be configured to secure the wearable computing device 400 to a user's face via a user's nose and ears, respectively. In certain implementations, each of the structural elements 402, 404, and 406 and the extending side-arms 412, 414 can be formed of a solid material such as plastic and/or metal. Alternatively, each of the structural elements 402, 404, and 406 and the extending side-arms 412, 414 can be formed of a hollow structure of similar material so as to allow wiring and component interconnects to be internally routed through the wearable computing device 400. It should be noted that a combination of solid and hollow components can be used together during the construction of the wearable computing device 400.

One or more of the lens elements 408, 410 can be formed of any material that can suitably display a projected image or graphic. For example, each of lens elements 408,410 can be manufactured from a plastic such as a thermoplastic polymer. In certain implementations, the lens elements can be made from a thermoplastic such as polycarbonate. Each of the lens elements 408, 410 can also be made from a material that is sufficiently transparent to allow a user to see through the lens elements 408, 410 such that the user can wear the wearable computing device 400 in their daily lives without unnecessary complications due to reduced visibility. Combining these two features of the lens elements may facilitate an augmented reality or heads-up display where the projected image or graphic is superimposed over a real-world view as perceived by the user through the lens elements.

The wearable computing device 400 can also include an on-board computing system 416, an image acquisition device such as video camera 418, and an input device such as a finger-operable touch pad 420. The on-board computing system 416 is shown to be positioned on the extending side-arm 412 of the wearable computing device 400; however, the on-board computing system 416 can be provided on other parts of the wearable computing device 400 or can be positioned remote from the wearable computing device 400 (e.g., the on-board computing system 416 could be wire- or wirelessly-connected to the wearable computing device 400). The on-board computing system 416 can include a processor and memory, for example. In certain implementations, the processor can include a single or multi-core processor designed as a system on a chip such that data processing, audio processing and video processing are performed by the same processor. The memory can include a read-only portion configured to store, for example, bios information used by the processor when booting or performing other critical functions. The memory can also include a read/write portion configured to store application data and related instructions, user created information such as audio and video recordings, still images, and other information that can be read from and/or written to memory. The on-board computing system 416 can be configured to receive and analyze data from the video camera 418 and the finger-operable touch pad 420 (and possibly from other sensory devices, user interfaces, or both including, for example, one or more accelerometers configured to measure position and movement information) and generate images for output by the lens elements 408 and 410.

The video camera 418 is shown positioned on the extending side-arm 412 of the wearable computing device 400; however, the video camera 418 can be provided on other parts of the wearable computing device 400. The video camera 418 can be configured to capture images at various resolutions or at different frame rates. Many video cameras with a small form-factor, such as those used in cell phones or webcams, for example, can be incorporated into wearable computing device 400. Additionally, a microphone can be included on the medical device 400 for recording audio associated with any video being capture in addition to audible commands from the user wearing the medical device 400.

Further, although FIG. 4 illustrates one video camera 418, more video cameras may be used, and each may be configured to capture the same view, or to capture different views. For example, the video camera 418 can be forward facing to capture at least a portion of the real-world view perceived by the user. This forward facing image captured by the video camera 418 can then be used to generate an augmented reality where computer generated images appear to interact with the real-world view perceived by the user.

The finger-operable touch pad 420 is shown on the extending side-arm 412 of the wearable computing device 400. However, the finger-operable touch pad 420 can be positioned on other parts of the wearable computing device 400. Also, more than one finger-operable touch pad can be included on the wearable computing device 400. The finger-operable touch pad 420 can be interacted with by a user to input commands. The finger-operable touch pad 420 can sense at least one of a position and a movement of a finger via capacitive sensing, resistance sensing, or a surface acoustic wave process, among other possibilities. The finger-operable touch pad 420 can be capable of sensing finger movement in a direction parallel or planar to the pad surface, in a direction normal to the pad surface, or both, and may also be capable of sensing a level of pressure applied to the pad surface. The finger-operable touch pad 420 can be formed of one or more translucent or transparent insulating layers and one or more translucent or transparent conducting layers. Edges of the finger-operable touch pad 420 can be formed to have a raised, indented, or roughened surface, so as to provide tactile feedback to a user when the user's finger reaches the edge, or other area, of the finger-operable touch pad 420. If more than one finger-operable touch pad is present, each finger-operable touch pad can be operated independently, and can provide a different function.

It should be noted that the wearable computing device 400 can be configured to operate independently or as an accessory device to another computing device such as device 200 as described above. For example, the wearable device can be configured to have a low power processor using a short-range communication protocol. In such an arrangement, the wearable device can be configured to operably connect to another computing device to take advantage of the greater processing power and communication abilities of the second computing device.

Sample Communications Network

Figure 5:
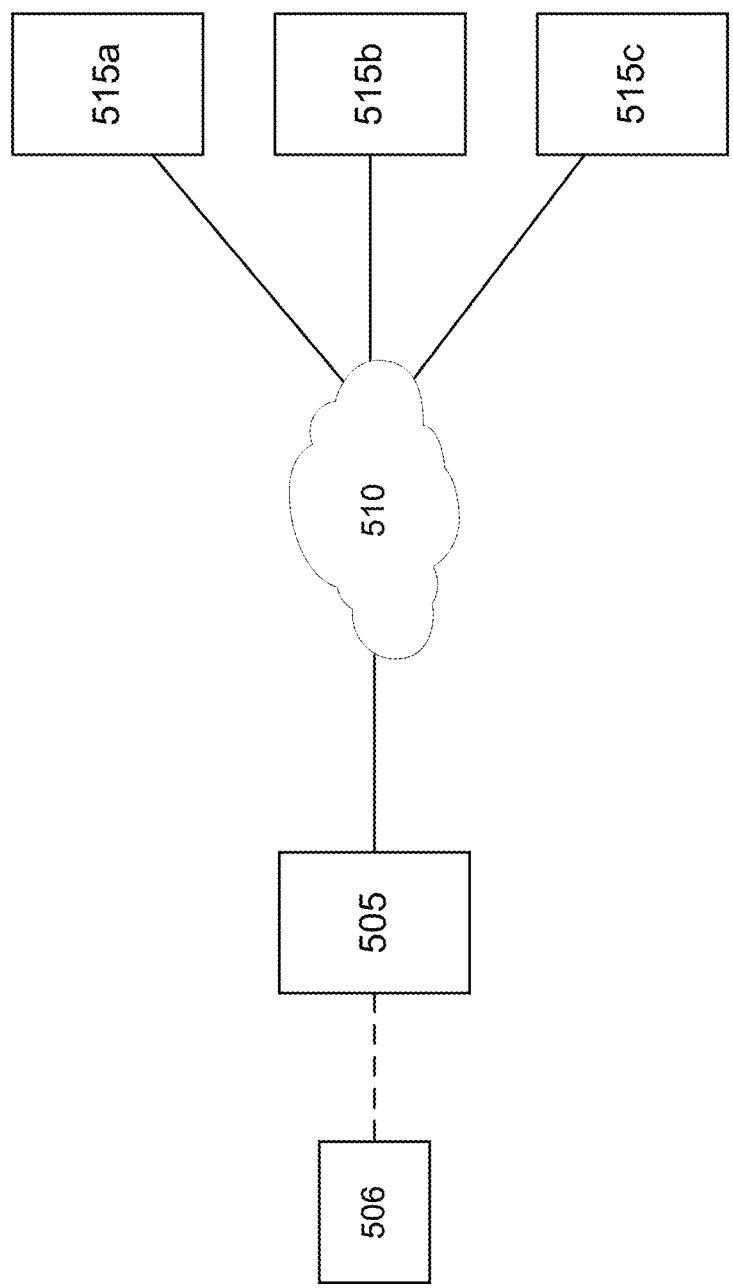
FIG. 5 depicts a sample network architecture, in accordance with an example of the present disclosure.

FIG. 5 illustrates a sample network 500 configured to implement various augmented reality capabilities such as those described herein. In the network 500, a portable computing device (e.g., device 200 as described above) can be operably connected to a communications network 510. For example, the communications network 510 can be a wide area network such as the Internet. In other examples, the communication network can be a local area network such as an intranet that provides metered or otherwise monitored access to an outside network such as the Internet. Various remote computers 515*a*, 515*b*, and 515*c* can also be operably connected to the communications network 510. As such, the portable computing device 505 can establish a data transfer connection with one or more of the remote computers 515*a*, 515*b*, 515*c*.

Additionally, an accessory device such as a wearable computing device 506 (e.g., wearable computing device 400 as described above) can be operably connected to portable computing device 505. However, as noted above, depending upon the communication and processing capabilities of the wearable computing device 506, the wearable computing device 506 can be configured to establish a direct connection to the network 510.

Patient-Based Augmented Reality Techniques

As noted above, augmented reality capabilities and functionality can be provided to a patient prescribed a wearable medical device to enhance the patient's experience. For example, a patient that has been prescribed a wearable medical device can also be given access to an application or portable medical device that is configured to provide the patient with additional contextual information related to their use of the wearable medical device. In certain implementations, the patient can access the application on a portable computing device such as a smartphone or tablet computing device (e.g., device 200 as described above). The application can be configured to receive a set of streaming images from an image acquisition device integrated into the portable computing device. The application can process the received streaming images to determine if one or more predetermined recognizable features are present in the streaming images. If the application determines that there are one or more predetermined recognizable features in the streaming images, the application can retrieve additional contextual information relating to the wearable medical device and augment the streaming images with the contextual information for display on the portable computing device.

In order to determine if the one or more predetermined recognizable features are included in the streaming images, the application can also include a library, or have access to a library via a remote computer, of recognizable features such as shapes, symbols, text, serial numbers, and other similar features. The application can be configured to perform a comparison and/or match of various features in the streaming images against the library to determine if one or more of the recognizable features are included in the streaming images. Such a process is described in greater detail in the discussion of FIG. 6 below.

Based upon the recognizable features, as well as a context of what environment the patient is in, the application can be configured to provide contextual information to the patient by augmenting the streaming images with the contextual information. For example, if the patient has their portable computing device articulated such that the image acquisition device is directed toward a monitoring component of the medical device, the application can identify the monitoring component (e.g., via a match of one or more recognizable features of the monitoring component), retrieve contextual information related to the monitoring component (e.g., software version information, network communication information such as signal strength, instruction information including instructional videos and how-to information), and augment the display of the patient's portable device with this information. Such an example is described in greater detail in the discussion of FIG. 7 below.

Additionally, the application can provide a gateway or portal for accessing technical support related to operation of the medical device. For example, a technical support specialist can also access the streaming images to identify what the patient is looking at (e.g., the medical device) and attempt to troubleshoot or identify any problems associated with the medical device. The technical support specialist can then augment the streaming images with additional information specific to that medical device for display on the portable computing device (associated with the patient) such that the patient receives the specific information.

Figure 8:
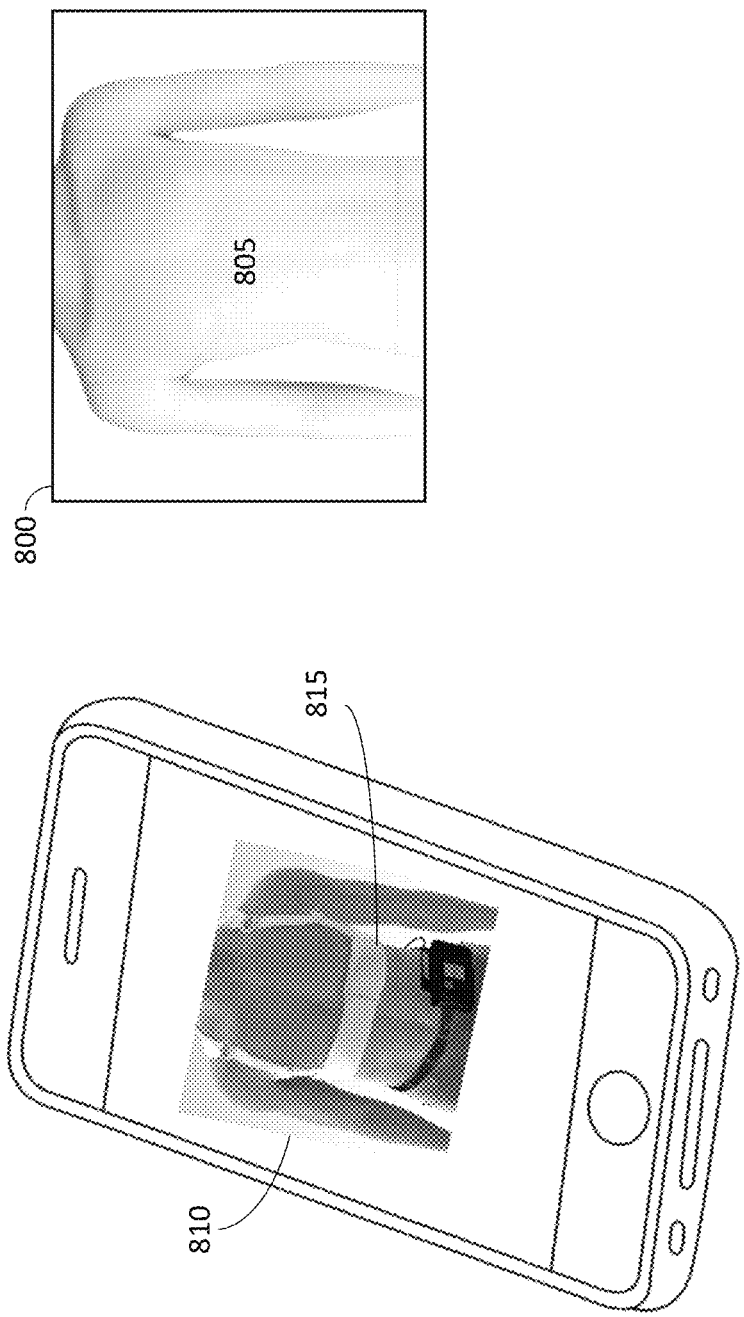
FIG. 8 depicts a sample view of fitting information related to a wearable medical device augmented onto the patient's computing device, in accordance with an example of the present disclosure.
Figures 9A, 9B:
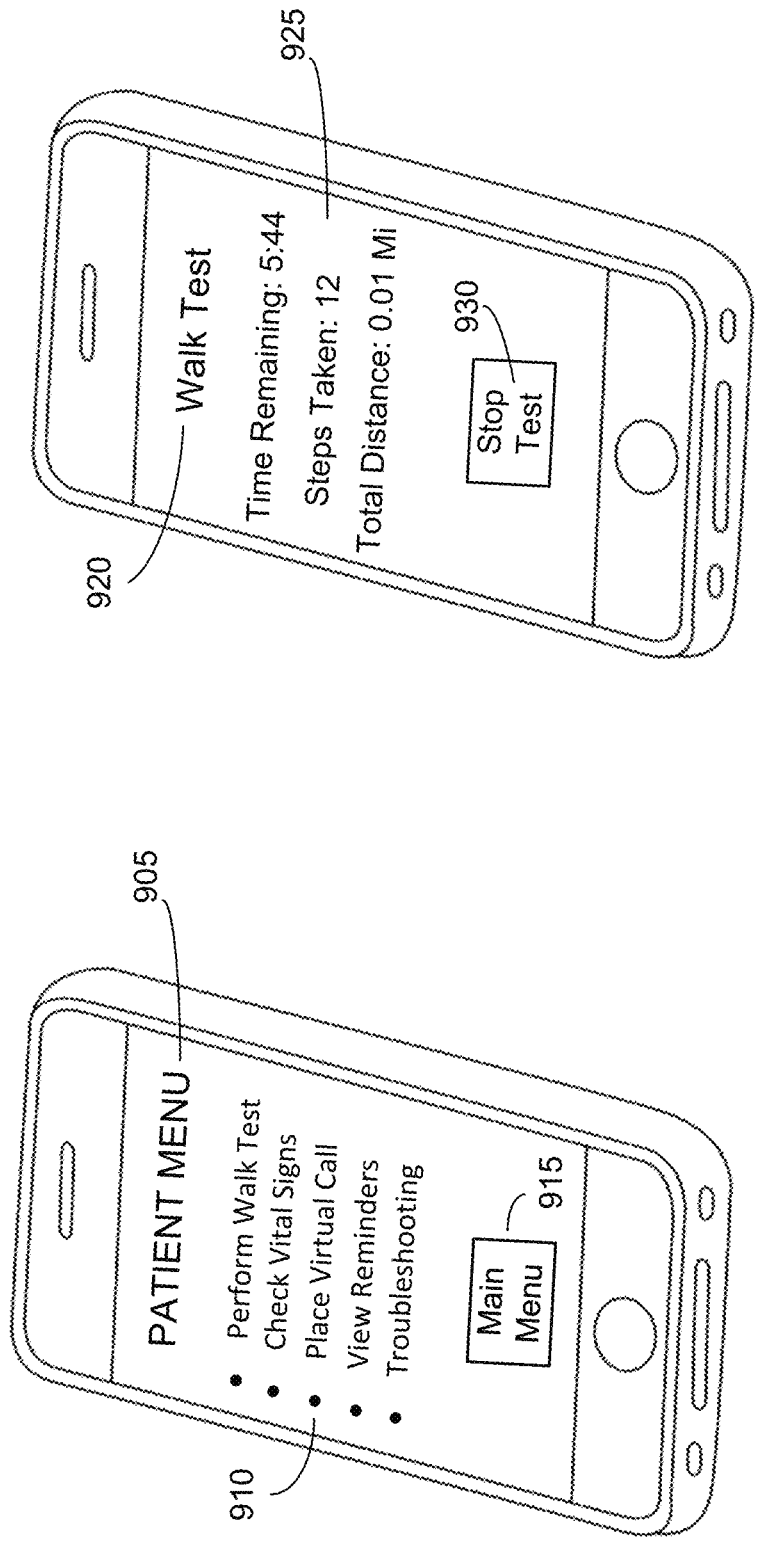
FIGS. 9A and 9B depict sample views of interactive patient features on a patient's computing device, in accordance with an example of the present disclosure.

In yet another implementation, the application can provide the patient with fitting information, or simulate what the patient would look like when wearing the medical device. Such an example is illustrated in FIG. 8 and described in detail below. In certain implementations, the patient can also access a patient menu that is configured to include one or more options for patient-specific activities and/or options for the patient to access while wearing the medical device. Examples of such implementations are illustrated in FIGS. 9A and 9B and described in detail below.

Figure 6:
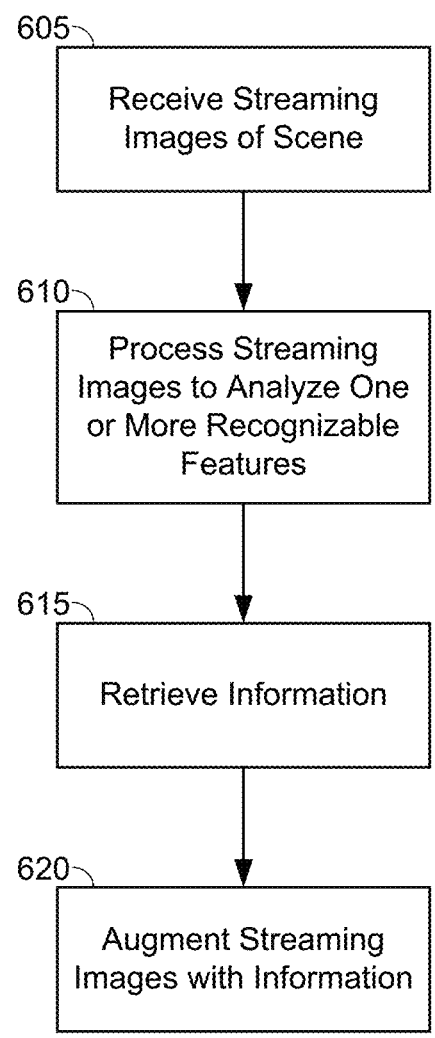
FIG. 6 illustrates a sample process for including augmented reality information on a patient's computing device, in accordance with an example of the present disclosure.

FIG. 6 illustrates a sample process for including augmented information into a display of streaming images on, for example, a patient's portable computing device. The patient can initiate the process by opening an application. For example, the application can be designed, programmed, and provided by the manufacturer of the medical device the patient has been prescribed. The application can include a set of instructions for causing various components of the patient's portable computing device to operate in concert to provide the patient with an augmented reality experience. For example, the application can cause an image acquisition device to begin acquiring a set of streaming images that can be displayed in real-time, or nearly in real-time, on a display or user interface of the portable computing device. The application can further instruct the processor to receive 605 the set of streaming images and process 610 the streaming images to analyze the images for one or more predetermined recognizable features that can be used to determine a context of the scene, e.g., in what environment is the patient and what is included in the set of streaming images.

When using an augmented reality system, various aspects such as feature recognition, combination of real and virtual data, interactivity in real or near-real time, and proper registration are used by a processing device to recognize one or more features and overlay information on or adjacent to those recognized features. In order to recognize a feature such as a specific shape or item, an augmented reality system typically uses camera calibration in combination with a high-level contrasting measurement configured to identify changes such as texture changes, coloration changes, size and shape changes, and other similar distinguishing aspects that can be used to define a feature such as an outline of an object. A library of information such as a database storing images or other representation of recognizable features can be accessible to the augmented reality system. For example, as described herein, a manufacturer of medical devices can create a library including images, shape data (e.g., measurement information such as length-width-height ratios), identifying symbols, and other data that can be analyzed to identify one or more recognizable features. The information contained within the library can be obtained for various views of the device, e.g., through a scan by a 360-degree camera or other similar device such as a 3D modeling scanner.

When receiving an image of a scene, the augmented reality system can be configured to identify multiple contrast points throughout the image such as, for example, lines delineating color and/or texture changes, fiduciary markers such as object corner markers, length-width-height indicators, object outlines, and other similar contrast points can be identified. The augmented reality system can them perform object recognition including specific objection recognition, feature detection and correspondence, and pose/position estimation. In certain implementations, the augmented reality system can implement the recognition process using a Bayesian network to determine object geometry which can then be matched against the library of recognizable features. Such a process is explained in greater detail in "Applying Object Recognition and Tracking to Augmented Reality for Information Visualization," by Silva et al., published by ResearchGate, June 2004, a copy of which is included as Appendix A, and the content of which is hereby incorporated by reference in its entirety.

Referring again to FIG. 6, processing 610 the streaming images can include comparing and/or matching the recognizable features to a library of stored features. In certain implementations, the processing 610 can include scanning the streaming images for a shape having one or more identified distinguishing features, comparing the one or more identified distinguishing features against a library storing information relating to a set of predetermined recognizable features, identifying a match between the one or more identified distinguishing features and at least predetermined recognizable feature, and identifying the wearable medical device based upon the match. For example, the processor can potentially identify various components of the medical device such as a medical device monitor, a battery, a garment, an electrode belt, a sensing electrode, and a therapy electrode.

Based upon the identified wearable medical device, the application can cause the processor to retrieve 615 additional and/or contextual information related to the medical device. For example, the processor can retrieve diagnostic component information (e.g., serial numbers, manufacturing dates, operating status, battery charge level) for the identified one or more components, operating instructions for the medical device, assembly instructions for assembling the wearable medical device, and other similar contextual information.

The application can then cause the processor to augment 620 the display of the streaming images with the retrieved information such that the augmented information is provided to the patient. When augmenting 620 the display of the streaming images, the application can track various parameters such as camera movement and calibration to maintain a high level of registration between the real world information contained within the streaming images and the virtual or augmented information overlaid in the streaming images. Various tracking mechanisms such as optical tracking, motion-based tracking, magnetic tracking, and other similar tracking mechanisms can be used by the application to track and calibrate camera movement. Additionally, based upon the computation capabilities of the computing device running the application, the camera can be calibrated for each frame captured, or at a reduced rate (e.g., every 2 frames, every 5 frames, or at a dynamic frame rate that changes based upon available computational resources).

Depending upon available resources, the application can track movement of one or more objects within the streaming images using various techniques. For example, the application can process an entire frame in the streaming images to locate and identify various objects contained within the streaming images. The full frame analysis can be done for each frame in the streaming images or at a reduced rate (e.g., every 2 frames, every 5 frames, or at a dynamic frame rate determined based upon available resources). The application can also process each frame to identify changes occurring within the streaming images on a frame-by-frame basis, e.g., identifying and recording specific object changes identified through measured contrast or color changes (e.g., by analyzing color and contrast information for each pixel in a frame as compared to color and contrast information from a previous frame). Similar to the full frame analysis, analysis using change information can be done for each frame or at a reduced rate. By using one or more movement tracking techniques along with camera calibration, the application can provide information overlaid within the streamlining images that is aligned with real world objects without compromising the visual impression that the two types of information (i.e., real world information and augmented information) coexist simultaneously and synergistically.

FIGS. 7 and 8 illustrate examples of providing a patient with specific augmented information.

FIG. 7 depicts an example of displaying additional information related to a medical device monitor 705 on a portable computing device by augmenting the display of the portable computing device to include the additional information. For example, as shown in FIG. 7, the portable computing device can be oriented such that an image acquisition device of the portable computing device is direct toward the monitor 705. An image 705 of the monitor can be displayed at real-time, or at near-real time, on a display or user interface (e.g., touchscreen) of the portable computing device. Additionally, as noted above, the processor of the portable computing device can scan the image 705 of the monitor 700 for any recognizable features. For example, the processor can scan the outline of the monitor 700 in the image 705 to identify which specific model of monitor 700 is displayed. Once identified, the processor can retrieve additional information such as operational information related to the monitor 700, instructions, software version information, and other related information. The processor can augment the images being displayed by the portable computing device. For example, as shown in FIG. 7, the image 705 can be augmented to include additional information 710, 715 and 720.

Depending upon the capabilities of the portable computing device, the additional information (e.g., additional information 715) can include multi-media files such as an instructional video or soundbite that includes instructions and/or information related to the operation of the medical device.

Additionally, as shown in FIG. 8, augmented reality techniques such as those described herein can be used to provide a patient with fit information related to a wearable medical device. Such a feature can be used by a doctor when prescribing a patient a wearable medical device (e.g., to provide a preview of what the device will look like when worn), by a patient service representative that is helping a patient be fit for a wearable medical device, or by the patient at a later time to refresh their memory of how the device is to be worn. In some implementations, the application can be configured to flip or reverse a patient's image to compensate for the reversal of the patient's reflection in the mirror such that components of the wearable medical device are appropriately positioned on the patient's image.

As shown in FIG. 8, the patient can stand in front of a mirror 800 such that their torso 805 (or whatever portion of their body that the wearable medical device will be worn on) is shown in the mirror. The patient can then capture an image 810 of their torso on a portable computing device. The augmented reality application can then augment the image 810 of the patient to include a representation 815 of the wearable medical device.

In addition to showing the wearable medical device on the patient, the augmented information can also include additional information that can be used to simulate operation of the medical device. For example, for a wearable cardioverter defibrillator, the augmented information can include a video or simulation of the monitor issuing an alarm, conductive gel deploying, and a therapeutic shock being delivered.

In addition to fitting and instructional information augmented onto a display of the patient's computing device as described above, the application can be configured to provide one or more interactive activities for the patient to access when wearing the medical device. FIG. 9A illustrates a sample view of a patient menu 905 as displayed on a patient's computing device such as, for example, a smartphone. The patient menu can include a list 910 of various tasks, activities, or functions that the patient has access to when wearing the medical device. For example, as shown in FIG. 9A, the list 910 can include perform a walk test, check vital signs, place a virtual call, view reminders, and troubleshooting. However, it should be noted that this list is provided by way of example only, and the actual list as shown in the patient menu can vary. In certain implementations, the patient menu can be set by the manufacturer of the medical device such that the patient has access to a predefined list of activities, tasks, and functions. In some examples, the list of tasks, activities, and/or functions that the patient has access to can be setup during the initial setup of the medical device by, for example, a physician or patient service representative.

Each task, activity, and/or function as listed in the list 910 can initiate or otherwise perform some function related to the patient, the wearable medical device, or a combination of the two. For example, perform walk test can be related to initiating timing and tracking functions for an industry accepted walk test such as the six-minute walk test. The perform walk test option is described in greater detail below in the discussion of FIG. 9B. Another option as listed in sample list 910 can include check vital signs. In certain implementations, this option can use sensing features of the wearable medical device to determine one or more vital signs of the patient and display these vital signs such as current heartrate to the patient on the patient's computing device. Another option can include place a virtual call. In certain implementations, this option can utilize features included in the application to place a call (e.g., voice only or video) to a caretaker, physician, family member or other person associated with the patient. In an implementation where the patient has the option to contact multiple people, selection of the place a virtual call option can open a sub-listing of possible contacts. The patient can also have the option to select and view any reminders. For example, the patient might be prescribed one or more prescription drugs to be taken on a regular schedule. The application can provide a reminder to the patient through the application when it is time to take their prescribed drugs. In some examples, the patient can use the view reminders option to see any upcoming reminders, set new reminders, cancel reminders, or other similar scheduling activities.

As shown in FIG. 9A, in certain implementations, the patient can access a troubleshooting option. As noted above, the application can be configured to provide a technical support interface. For example, the application can cause the processor to establish a communication session with a remote communications device such as a technical support server or computer, receive device information such as troubleshooting information from the remote communication device, and augment the received streaming images with the device information. In such an example, the troubleshooting information can include a set of instructions for the patient to perform.

In some implementations, the troubleshooting information can include a pre-recorded audio and/or video presentation for the patient to view that is, for example, loaded on-demand during a troubleshooting session from a library of media.

As shown in FIG. 9A, the patient menu 905 can also include a button or other selectable area 915 for returning to, for example, a main menu. Upon selection of button 915, the application can return to a main menu or other similar initial interface until the patient selects another option.

Patient-Based Use Examples

In various implementations, the augmented reality techniques as described herein can be used to provide additional information to a patient prescribed a wearable medical device at various points throughout their time wearing the device. At various points throughout their experience with a wearable medical device, multiple occasions to use the augmented reality techniques as described herein can be incorporated to improve the quality of the patient's experience wearing the device.

For example, a physician such as a cardiologist can prescribe a patient a wearable medical device such as a wearable cardiac monitoring device or a wearable cardioverter defibrillator (WCD) such as the LifeVest. When prescribing the device, the physician can provide the patient with a device such as a tablet computing device or a wearable computing device such as an augmented reality headset. The patient, or another caregiver such as a nurse associated with the physician, can use the device to visually simulate wearing the wearable medical device. For example, the physician can open an augmented reality application provided by a manufacturer of wearable medical devices. The physician can enter a prescribing mode where they select from a list of devices that can be prescribed to the patient. For example, if the physician is prescribing a wearable cardiac monitor, the physician can select a specific model of wearable cardiac monitor from a list such as a drop-down list in the augmented reality application. Depending upon the interface that will be provided to the patient (e.g., a portable computing device such as a tablet computing device or a wearable computing device such as an augmented reality headset), the physician can access the application via a portable computing device such as a notebook or tablet computer, or via a desktop computer (e.g., a desktop computer operably connected to the wearable computing device).

The augmented reality application can then retrieve information related to the selected wearable medical device such as images, videos, instructions for use, insurance/payment information, instructions for cleaning and care of the wearable medical device, and other related information for review by the physician and the patient. As such, prior to receiving the wearable medical device, the patient can access various information related to the device and ask any questions that the information might prompt.

Additionally, similar to the discussion of FIG. 8 above, the physician can use the augmented reality application to provide a visual simulation of how the wearable medical device will be worn, and what the patient will look like wearing the device. For example, the patient can be given a wearable computing device to put on, the wearable computing device running a local version of the augmented reality application and/or being operably connected to a computing device (e.g., a desktop computer) that is running a version of the augmented reality application. The patient can then look into a mirror as described above. The augmented reality application can analyze a set of streaming images captured by an image capture device integrated into the wearable computing device to identify the outline of the patient's body as well as one or more additional features such as the patient's waist, the patient's chest, and other similar body features. The augmented reality application can retrieve information related to the wearable medical device such as an interactive image of the wearable medical device. The augmented reality application can alter the image such that it is appropriately sized and positioned on the patient's body as captured in the set of streaming images. The augmented reality application can overlay the wearable medical device image on the patient's body in the streaming images such that the streaming images being displayed to the patient on the wearable computing device are augmented to include a visual simulation that the patient is wearing the wearable medical device.

In certain implementations, the patient can also look down at their own body to see an overlay of one or more components of the wearable medical device as it would appear if it was being worn by the patient. In such an example, rather than merely providing an augmented reflection of the patient, the patient can view a real-time visual simulation of what the individual components would look like when being worn.

Additionally, the patient can receive instructions about assembly of the wearable medical device during a visual simulation. For example, if the wearable medical device includes electrode patches, the patient can view a video showing proper patch placement, the video being augmented such that the patient sees the proper placement of the patches on their own body as the video plays.

In addition to providing a visual simulation of wearing the wearable medical device, the augmented reality application can also provide a simulation of medical device operation. For example, if the wearable medical device is a WCD, the application can include a visual simulation of an alarm and treatment sequence associated with the device. In certain implementations, the patient, using, for example, a wearable computing device as noted above, can be immersed in the alarm and treatment sequence. For example, an alarm can be emitted by a speaker integrated into the wearable computing device that a treatment sequence is about to be initiated. The patient can then look down at where a monitor, for example, of the WCD would be worn. The augmented reality application can overlay an image of the monitor in an alarm state, e.g., displaying an appropriate message or visible indications as the monitor would in a real alarm and treatment sequence. The augmented reality application can be configured to provide multiple progressions of events as well. For example, the augmented reality application can be configured to display what the monitor would look like if the alarm is canceled or otherwise stopped. Additionally and/or alternatively, the augmented reality application can be configured to continue the alarm until the alarm portion of the sequence is completed.

Following the alarm, the augmented reality application can continue through the alarm and treatment sequence. For example, for a WCD, the augmented reality application can simulate release of a conductive gel prior to therapeutic shock delivery. This simulation can include a visual indication of gel flow at or around the therapy electrodes as displayed by the wearable computing device. After gel release, the augmented reality application can simulate delivery of the therapeutic shocks by, for example, flashing the images of the therapy electrodes.

In certain implementations, the simulation of the medical device operation can include audio information related to the alarm and treatment sequence, the audio information explaining to the patient exactly what is occurring. For example, for a WCD, immediately after the alarm sounds, recorded information can be played providing an overview of the alarm portion of the sequence. As the sequence progresses toward treatment, the audio information can provide updated information explaining what portion of the sequence is occurring, e.g., during gel deployment and then during therapeutic shock delivery. The audio information can also provide an explanation of what should occur after a treatment.

In addition to providing information to a patient, the augmented reality application can be configured to provide information to one or more people associated with the patient such as a spouse, child, personal caregiver, or other similar people. For example, a spouse can use the portable computing device as described above to view information related to proper assembly and wearing of the wearable medical device, what occurs during a treatment sequence, and other related information such as instructions for device cleaning and care.

It should be noted that the above description of the physician and patient interaction using the augmented reality application is described as being implemented using a wearable computing device by way of example only. In certain implementations, a portable computing device such as a tablet computing device can be used. In other implementations, the physician can provide instructions for the patient to install the augmented reality application on their personal device such as a smartphone or tablet computer. Additionally, a computing device such as a table computer can be provided to the patient for use while they are prescribed the wearable medical device, thereby providing the patient with access to the additional information as described above.

Following the above description of the physician and patient interaction using the augmented reality application, the physician can prescribe the device to the patient. The patient can receive the device from a service representative of, for example, the manufacturer of the wearable medical device or another similar person capable of properly fitting the wearable medical device and providing instructions for its use. As before, an augmented reality application can be used to provide the patient with additional information. For example, similar as above, the augmented reality application can be accessed on a wearable computing device and/or a portable computing device provided by the service representative or belonging to the patient (or, as noted above, prescribed to the patient during their use of the wearable medical device). Based upon the patient's level of interest and information retained from the physician interaction, the service representative can repeat the wear simulation as well as the simulated alarm and treatment sequences. Additionally, the service representative can access additional features related to more specific topics related to the interaction between the patient and the wearable medical device. For example, the service representative can select a set of assembly and wear instructions for the patient to view that are specifically designed for the model and components that the patient is being fitted with. Such instructions can be displayed on, for example, a wearable computing device by the augmented reality application during actual assembly and fitting of the wearable medical device. Such an approach can also provide the manufacturer of the wearable medical device is assurance that consistent instructions are being provided to each patient prescribed the same wearable medical device.

Additionally, the augmented reality application can be configured to interact with the patient during the fitting. For example, the augmented reality application can be configured to step through various screens as displayed on the monitor to provide the patient with an overview of what each screen means, when to do when a particular screen is displayed, and how to access various features such as the help menu and access to troubleshooting information. In certain implementations, in order to establish a baseline for cardiac monitoring, the patient can be instructed to perform a physical test such as a timed walk test. During the physical test, the augmented reality application can be configured to provide additional instructions to the patient, ask the patient questions related to how they are feeling during the test, and provide updated information related to results of the test. Various input devices such as touchscreen interfaces, microphones, accelerometers, eye-movement measuring device, and other input devices can be used to measure patient responses during such an interaction.

In certain implementations, the augmented reality application can establish an initial troubleshooting or service session to verify that the wearable medical device is operating properly prior to the service representative leaving the patient. For example, the augmented reality application can be configured to establish a real-time communication session with a technician or support specialist associated with the wearable medical device manufacturer. The support specialist can then instruct the patient to look at various components of the wearable medical device such as the monitor, sensing and/or therapy electrodes or electrode patches, a battery charger, a communications module such as a data hotspot, and other similar components. The augmented reality application can be configured to provide overall contextual information related to each of these components as the patient looks at each, as well as to provide the support technician with a chance to verify that the components are properly positioned and operating.

Following the prescription and fitting of the wearable medical device, the patient can also use the augmented reality application during their use of the device to provide them with additional device information, instructions, and troubleshooting information. As noted above, a version of the augmented reality application can be installed on a portable computing device associated with the patient, whether it is the patient's own device such as a tablet computing device or a smartphone, or a device loaded or otherwise provided to the patient during their use of the wearable medical device. The patient version of the augmented reality application can include a limited functionality as compared to the physician and service representative versions. For example, the patient version can be locked to the patient's specific wearable medical device model and cannot be changed by the patient. Additionally, information available to the patient can be filtered to prevent sensitive information such as detailed setup instructions from being available to the patient.

As described above in regard to FIG. 7, the patient can use the augmented reality application to obtain information related to the operation of the wearable medical device. For example, the patient can open the augmented reality application on a specific portable computing device and direct an image acquisition device integrated in the portable computing device a component of the wearable medical device such as the monitor. The augmented reality application can identify the monitor in a set of streaming images and retrieve additional information related to the monitor such as software version information, battery information, connectivity status information, and operational information such as instructions for using the monitor (including multimedia files such as videos and audio files related to the monitor). In such an example, the patient can refresh their memory about proper use of the wearable medical device independently without contacting their service representative or technical support.

If the patient is having problems with the wearable medical device, the augmented reality application can be used to establish a troubleshooting session with a service representative associated with the manufacturer of the wearable medical device. As noted above, the troubleshooting session can include two-way communications such that the support specialist can access the set of images being captured by the patient's computing device. The support specialist can then provide the patient instructions for additional steps to take to troubleshoot a problem. For example, the support specialist can instruct the patient to direct the image acquisition device at the monitor. The support specialist can then either remotely access the monitor to perform one or more tests (while watching the results of the tests in near real-time via the augmented reality application), or provide the patient with instructions to perform one or more tests (e.g., access a test via manipulation of one or more input devices associated with the monitor). In a similar implementation, the support specialist can use the two-way communication to have the patient direct the image acquisition device at themselves to see if the patient has properly assembled the wearable medical device. The support specialist can provide feedback to the patient via the augmented reality application such as proper electrode patch positioning, the feedback being overlaid on the display of the patient's computing device such that the patient can view the feedback information.

Additionally, in certain implementations, the patient can access a list of tasks, activities, and/or functions associated with wearing the medical device. See, for example, FIG. 9A and the accompanying description as provided above. In some examples, the patient's physician can instruct the patient to perform certain activities on a regular schedule, e.g., perform a daily walk test. The application can be configured to provide the patient with augmented information related to this activity. FIG. 9B illustrates an example of using the application to provide a patient with information related to an ongoing walk test. As shown in FIG. 9B, when the patient is performing the walk test, the patient's computing device (e.g., a smartphone) can display information relevant to the walk test. For example, the application can list various information 925 such as time remaining in the walk test (e.g., if the patient is performing a six minute walk test), steps taken during the walk test, total distance traveled during the walk test, and other similar data. In certain implementations, the application can also provide a patient-selectable button 930 for stopping the test prior to the test's completion. It should be noted that a timed walk test is provided by way of example only and, in certain implementations, a distance-based walk test can be used. For example, the patient can be instructed to walk half a mile. In such an example, the information 925 can be altered to include additional details such as time elapsed, total steps taken, and distance remaining.

Upon completion of the walk test, the application can be configured to provide final statistics to the patient (e.g., total steps taken, total distance covered) as well as historical information for comparison purposes (e.g., a comparison of total steps taken in the most recent test as compared to an average of total steps taken in all previous walk tests). In certain implementations, the application can also query the patient about various aspects of the walk test and their current condition following the walk test. For example, the application can display questions related to shortness of breath, overall fatigue, pain or numbness in the legs or other extremities, and other similar health related questions. The application can be configured to receive patient answers to the questions and locally or remotely store the information in a patient diary for review by a caregiver or physician.

It should be noted that the above patient-based use scenarios are provided by way of example only. Various details such as devices used, participants involved in both viewing and providing the information, and other similar details can be altered or changed accordingly depending upon the implementation of the augmented reality techniques as described herein. It should also be noted that the techniques as described herein are not merely limited to augmented reality. Additional immersive technologies such as virtual reality can be utilized as well. For example, during the alarm and treatment sequence, a virtual reality headset can be used to fully immerse the patient in the simulation, including full visual, audio and haptic feedback.

Caregiver-Based Augmented Reality Techniques

As noted above, augmented reality capabilities and functionality can be provided to a nurse or other similar caregiver caring for a patient that has been prescribed a wearable medical device. For example, a caregiver associated with the patient can have a similar portable computing device (e.g., a wearable computing device such as an augmented reality headset) for receiving information related to both a medical device as well as a patient associated with the medical device. For example, a caregiver application can be configured to process a set of streaming images to determine one or more predetermined recognizable features in the images to determine both the medical device as well as a patient using the medical device. For example, there can be a QR code, barcode, or other similar symbol associated with the medical device that can be included in the streaming images. In certain implementations, the caregiver application can be configured to identify an outline of a portion of a patient's body such as a patient's head and face. In some examples, the caregiver application can perform a facial recognition process using, for example, a standard facial recognition algorithm to identify the patient. The caregiver application can then retrieve information specific to that medical device and/or patient and augment the streaming images such that the information is provided to the caregiver.

For example, in a hospital setting, a nurse can have an augmented reality headset. The nurse can enter a patient's room, look at their medical device (or another similar feature that would be recognizable to the caregiver application), and the caregiver application can identify the medical device, the associated patient, and access current physiological data related to the patient for display to the nurse. In certain implementations, the nurse can direct their augmented reality headset such that it is capturing images of the patient. The images of the patient can be analyzed such that the caregiver application can identify the patient (e.g., via a recognition process such as a facial recognition process). Additionally, the identification of a device and/or patient can be supplemented with additional information such as location information. For example, the location of the nurse can be identified through positioning techniques such as WI-FI network tracking, global positioning system tracking, and other similar positioning techniques. Examples of processes for identifying a wearable medical device and/or a patient wearing a wearable medical device is described in greater detail in the discussion of FIGS. 9 and 10 below.

Figure 10:
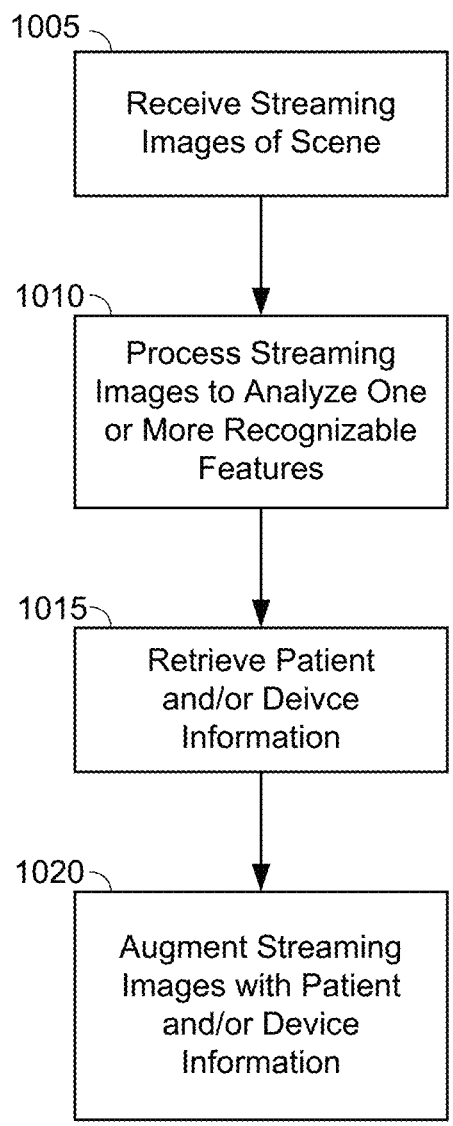
FIG. 10 a sample process for including augmented reality information on a caregiver's computing device, in accordance with an example of the present disclosure.

FIG. 10 illustrates a sample process for included augmented information into a display of streaming images on, for example, a nurse's portable computing device. The nurse can initiate the process by opening an application. For example, the application can be designed, programmed and provided by the manufacturer of the medical device that one or more patients been prescribed. The application can include a set of instructions for causing various components of the nurse's portable computing device to operate in concert to provide the patient with an augmented reality experience. For example, the application can cause an image acquisition device to begin acquiring a set of streaming images that can be displayed in real-time, or nearly in real-time, on a display or user interface of the portable computing device. The application can further instruct the processor to receive 1005 the set of streaming images and process 1010 the streaming images to analyze the images for one or more predetermined recognizable features that can be used to determine a context of the scene, e.g., which patient is the nurse currently visiting or providing care to. For example, the nurse can scan or otherwise capture an image of a symbol associated with the patient that is placed on the patient's chart or the patient's wearable medical device.

Similar to above, processing 1010 the streaming images can include comparing and/or matching the recognizable features to a library of stored features. In certain implementations, the processing 1010 can include scanning the streaming images for a shape having one or more identified distinguishing features, comparing the one or more identified distinguishing features against a library the predetermined recognizable features, identifying a match between the one or more identified distinguishing features and at least predetermined recognizable feature, and identifying the wearable medical device and associated patient based upon the match. For example, the processor can potentially identify a QR code in the streaming images and determine, based upon processing of the QR code, which patient and/or medical device is associated with the QR code. In certain implementations, the processor can identify an outline of at least a portion of a patient's body such as the patient's head and face. The processor can use a recognition algorithm such as a facial recognition algorithm to identify or confirm the identity of a patient wearing the wearable medical device.

Based upon the identified wearable medical device and its associated patient, the application can cause the processor to retrieve 1015 additional and/or contextual information related to the medical device as well as patient specific information such as physiological information or operational information related to the current operational status of the wearable medical device. The patient specific information can be provided in real-time or at near real-time such that the nurse is accessing current information for the patient and/or the wearable medical device.

Figure 11B:
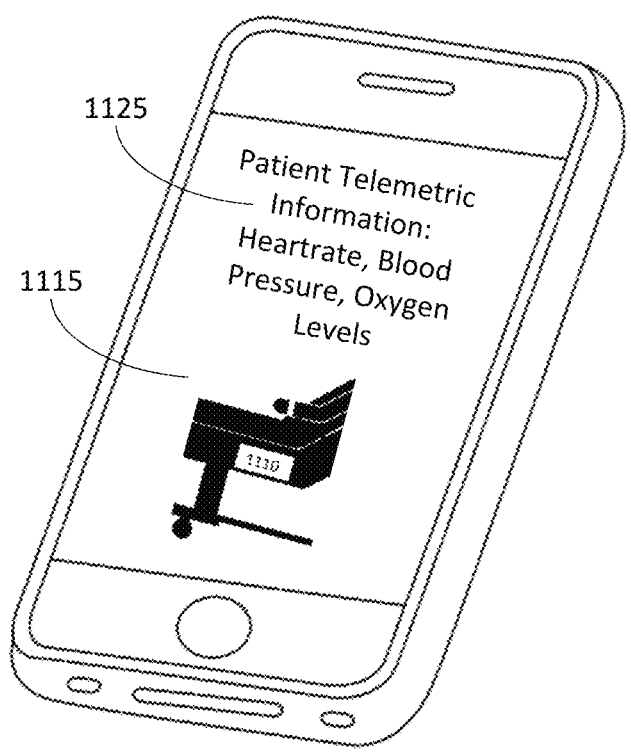

The application can then cause the processor to augment 1020 the display of the streaming images with the retrieved information such that the augmented information is provided to the patient. FIGS. 11A and 11B illustrate examples of providing a nurse with specific augmented information related to a patient and the patient's associated medical device.

FIG. 11A depicts an example of displaying additional information related to a patient on a nurse's portable computing device by augmenting the display of the portable computing device to include the additional information. Additionally, as shown in FIG. 11A, additional information can also be displayed on an optional wearable computing device such as wearable computing device 400 as described above.

For example, as shown in FIG. 11A, the portable computing device can be oriented such that an image acquisition device of the portable computing device is directed toward the patient 1105. More specifically, in certain implementations, the portable computing device can be oriented such that it is directed toward a symbol or other identifying feature 1110 associated with at least one of the patient 1105 and a medical device associated with the patient, e.g., a cardiac monitoring device. An image 1115 of the patient 1105 and/or feature 1110 can be displayed at real-time, or at near-real time, on a display or user interface (e.g., touch-screen) of the portable computing device. Additionally, as noted above, the processor of the portable computing device can scan the image 1115 for any recognizable features. For example, the processor can scan the feature 1110 and identify which specific patient is associated with the feature 1110. Once identified, the processor can retrieve additional information such as current physiological information related to the patient, historical patient information, operational information related to the patient's medical device, and other related information. The processor can augment the images being displayed by the portable computing device. For example, as shown in FIG. 11A, the image 1115 can be augmented to include additional information 1120 and 1125. Additionally, a display of the wearable computing device can be augmented to include additional information 1130. Information can be prioritized based upon importance and sensitivity. As the display of the wearable computing device is likely to only be visible to the nurse wearing the wearable computing device, sensitive information such as the patient's medical history can be displayed on the wearable computing device.

In certain implementations, the additional information 1120 and 1125 can include patient specific information such as a patient's physiological information. For example, as shown in FIG. 11B, the image 1115 can be overlaid in real-time with current values for various patient physiological and telemetric information such as a patient's heartrate, blood pressure, oxygen levels, temperature, and other similar physiological information. In certain implementations, the caregiver's computing device, and the monitoring application running thereon (including augmented reality capabilities), can operably connect to a telemetry monitoring system to obtain the patient's physiological information. The monitoring application running on the caregivers computing device (e.g., a smartphone or smart glasses as described above) can overlay the patient's information on the device's display, thereby providing the caregiver with access to the patient's information. As the caregiver moves to another patient (e.g., in another room), that patient can be identified by the monitoring application (e.g., similar to the process as described in regard to FIG. 10), and updated physiological and telemetric data can be displayed for the newly identified patient.

Beyond that as described above, additional functionality can also be incorporated into a wearable computing device worn by a nurse or other caregiver. For example, in a hospital setting, if an alarm occurs for a patient that is associated with a particular nurse, that nurse can receive an augmented alert on their wearable computing device, the alert including real-time physiological information for the patient, the type of alarm occurring, the patient's location and other information that might be critical to getting the patient immediate help. In some implementations, the caregiver can access an alarm history that includes, for example, a listing of all previous alarms issued by the patient's wearable medical device. The augmented reality system can then recreate each alarm along with any appropriate audio or video information related to the alarm, with real-time sequencing and timing similar to the actual alarm being issued.

In certain implementations, a wearable computing device can include an application or related functionality for providing the wearer, e.g., a nurse, with information for assisting a patient with application of various components of a wearable medical device. For example, if a patient is wearing a cardiac monitoring device that includes adhesive sensing electrodes, a related application can provide augmented information such that, when the nurse looks at the patient, locational information related to the placement of the electrode patches is provided to the nurse. This information can assist the nurse in being sure that the patches are positioned properly on the patient. Such an augmented reality scenario would be similar to FIG. 8 as described above.

Caregiver-Based Use Examples

In various implementations, the augmented reality techniques as described herein can be used to provide additional information to a caregiver associated providing care to one or more patients. For example, as noted briefly above, a nurse working in a hospital can be provided with a computing device such as a wearable computing device (e.g., an augmented reality headset as described above) that is configured to run an augmented reality application. The augmented reality application can be configured to provide the nurse access to additional information such as patient specific information in a timely and orderly manner.

In certain implementations, the nurse can access a listing of all their currently assigned patients. Using an input device such as a touchscreen or other similar touch sensor, the nurse can scroll through the listing to select a single patient. The augmented reality application can then access additional information related to the patient such as demographic information, real-time telemetric monitoring information such as ECG signals, blood pressure information, temperature information, pulse-ox information, and other physiological information. The nurse can also look at scheduling information for the patient such as feeding schedule information, medication scheduling information, upcoming or previous surgery information, and other related information. The augmented application can provide the nurse with an interface to communicate with other departments as well. For example, the nurse can initiate communications with a pharmacy via the augmented reality application to check on the status of a patient's medication.

Such an interface provides the nurse with a real-time interface to access patient specific information for each of their assigned patients at multiple locations where, for example, the wearable computing device can establish a secure data connection. The augmented reality application as described herein can also be configured to provide a nurse, or other similar caregiver, with access to additional information for one or more individual patients as well.

For example, similar to the description provided above in regard to FIGS. 11A and 11B, the nurse can wear a wearable computing device into a patient's room. The wearable computing device can be configured to run a version of a patient's monitoring application that includes, as described above, augmented reality features. Upon walking into the patient's room, the nurse can look at or otherwise scan an identification feature such as a symbol (e.g., barcode or QR code) printed on the patient's chart or another easily accessible location. The monitoring application can decode the symbol and, using information contained therein such as a patient identification number or other similar alphanumeric string, can access additional information related to that patient. For example, the information can include demographic information, real-time monitoring information such as ECG signals, blood pressure information, temperature information, pulse-ox information, and other physiological information. This information can be overlaid on the wearable computing device such that it is unobtrusively displayed to the nurse.

Additionally, the patient can have a prescribed wearable medical device such as a cardiac monitor that they are currently wearing. The nurse can scan an indicator on the wearable medical device, thereby causing the monitoring application to access information specific to that wearable medical device. Alternatively, in some implementations, the wearable computing device can open a new application specifically related to the wearable medical device (or open a separate plug-in module in the monitoring application).

In certain examples, rather than have the nurse scan an identifying symbol or marker, various local area communication protocols can be used to identify which patient or medical device is being selected. For example, an RFID tag can be associated with the patient and/or the wearable medical device that the nurse can scan. Upon scanning the tag, the wearable computing device can open the appropriate application to access the additional information. Similarly, a short-range communication protocol such as Bluetooth can be used to establish a communication link between the nurse's computing device and the patient's wearable medical device. The communication link can be used to provide identification information from the wearable medical device to the nurse's device for identification of the wearable medical device and/or the patient. A similar communication protocol such as mesh networking protocols (e.g., Zig-Bee®), infrared, near-field communications, and other similar protocols can be used to establish a communication link between a wearable medical device and the nurse's computing device.

Once the link has been established, or the wearable medical device has otherwise been identified, the nurse can access specific patient information from the device such as monitoring information (including, for example, ECG information), signal quality information, adhesive patch replacement information, and other related information. Additionally, when replacing or otherwise adhering an electrode patch, or placing a dry electrode on a patient, the nurse can be provided with a display of proper placement information overlaid on their view of the patient by the wearable computing device. Thus, wear information and instructions can be provided to a nurse or other caregiver that might not be adequately trained for a specific medical device.

To assist in establishing a communication link, or to help with finding a wearable medical device, the nurse's computing device can access positioning information related to the wearable medical device as measured, for example, by a GPS transceiver integrated into the wearable medical device. Such positioning information can be used to locate the last known placement of the device (e.g., if a patient has lost their wearable medical device), and location information can be displayed on the nurse's (or another similar person's) computing device. In some implementations, the nurse or similar caregiver can use the location information to locate a specific component of the wearable medical device. For example, the patient may indicate that they lost a battery charger or other similar component related to the wearable medical device. The nurse or caregiver can use the location information for that component to locate the missing component. Similar techniques can be used by device recovery personnel (e.g., employed by a medical device manufacturer or leasing agent) to locate and recover equipment from patients who are no longer being prescribed a wearable medical device but have not yet returned the device.

In some implementations, the augmented reality system can be configured to provide just-in-time instructions to a user. The instructions can be provided on demand (e.g., in response to a request by the user) or in real-time as a situation dictates. Specific instructions can be tailored, for example, to different models of a medical device, as functions and features change. For example, if a device is recalled, the user can be notified of any devices that were affected or if a specific device that a user is interacting with is subject to a recall. In some implementations, the augmented reality system can provide timeline information for a medical device such as, for example, whether a medical device is reaching the end of its in-service date or if a device has been misused or improperly stored.

It should be noted that the above caregiver-based use scenarios are provided by way of example only. Various details such the applications used for accessing and viewing the information can be altered or changed accordingly depending upon the implementation of the augmented reality techniques as described herein. Additionally, the computing device as described in the caregiver-based use examples was described as a wearable computing device by way of example only. A caregiver can access similar augmented reality features and applications on another type of portable computing device such as a smartphone or tablet computing device.

The invention claimed is:

1. An augmented-reality system for providing information, the system comprising:
   a wearable medical device configured to be worn by a patient on a body of the patient, the wearable medical device comprising
      at least one electrocardiogram (ECG) sensor coupled to the patient and configured to sense at least one ECG signal for the patient,
      a controller operably coupled to the at least one ECG sensor and configured to
         receive the at least one ECG signal from the at least one ECG sensor, and
         produce one or more cardiac parameters for the patient based upon the at least one ECG signal,
      at least one therapy electrode configured to couple to the patient and operably coupled to the controller, the at least one therapy electrode configured to produce, based upon the one or more cardiac parameters, a therapy shock,
      an electrode belt, and
      a garment comprising the electrode belt, the at least one ECG sensor, and the at least one therapy electrode; and
   an augmented-reality enabled computing device comprising
      an image acquisition device,
      a display operatively coupled to the image acquisition device, the display configured to receive and display a video of a scene having one or more predetermined recognizable features, and
      a processor operably connected to the display, the processor configured to execute one or more computer-readable instructions to cause the processor to
         receive the video of the scene, the video comprising the wearable medical device,
         process the video to analyze the one or more predetermined recognizable features to detect a presence of the wearable medical device within the scene, wherein the recognizable features define at least one of a plurality of components of the wearable medical device, the plurality of components comprising the at least one ECG sensor, the controller, the at least one therapy electrode, the electrode belt, and the garment,
         process the video to determine a context of the scene comprising an environment of the wearable medical device and at least one of the plurality of components of the wearable medical device, retrieve contextual information relating to the wearable medical device and the at least one of the plurality of components of the wearable medical device based on the context of the scene, the contextual information comprising at least operational information relating to the at least one of the plurality of components of the wearable medical device, and activity information related to a walk test the patient is performing, wherein the processor is configured to query the patient wearing the wearable medical device to answer one or more questions upon completion of the walk test, the one or more questions comprising questions related to shortness of breath, overall fatigue, and pain or numbness in extremities of the patient, and based on the retrieved contextual information relating to the wearable medical device and the at least one of the plurality of components of the wearable medical device, augment the received video with at least a portion of the contextual information relating to the wearable medical device and the at least one of the plurality of components of the wearable medical device such that at least a portion of the operational information related to the at least one of the plurality of components of the wearable medical device and at least a portion of the activity information is overlaid on the video of the scene and displayed on the display.

2. The system of claim 1, wherein the processor is configured to process the video to analyze the one or more predetermined recognizable features to detect the presence of the wearable medical device within the scene by:
scanning the video for a shape having one or more identified distinguishing features;
comparing the one or more identified distinguishing features against a library of the one or more predetermined recognizable features;
identifying a match between the one or more identified distinguishing features and at least one predetermined recognizable feature; and
identifying the at least one of the plurality of components of the wearable medical device based upon the match.

3. The system of claim 2, wherein the one or more identified distinguishing features comprises at least one of a barcode, a serial number, a QR code, and an identified physical shape of at least one component of the wearable medical device.

4. The system of claim 1, wherein the contextual information further comprises diagnostic component information for the at least one of the plurality of components of the wearable medical device.

5. The system of claim 1, wherein the contextual information further comprises instructions for a user of the augmented-reality enabled computing device to orient the augmented-reality enabled computing device such that the image acquisition device is directed to the at least one of the plurality of components of the wearable medical device.

6. The system of claim 5, wherein the processor is further configured to:
retrieve component information related to the at least one of the plurality of components of the wearable medical device; and
augment the received video with the component information.

7. The system of claim 1, wherein the augmented-reality enabled computing device is configured to provide, via the display, an interactive experience simulating operation of the wearable medical device.

8. The system of claim 7, wherein the interactive experience comprises simulating a fibrillation and treatment event.

9. The system of claim 1, wherein the one or more predetermined recognizable features comprises an outline of at least a portion of the body of the patient and the processor is further configured to detect a presence of the patient based on the one or more predetermined recognizable features.

10. The system of claim 1, wherein the contextual information further comprises operating instructions for the wearable medical device, and wherein the operating instructions are overlaid on the video of the scene and displayed on the display.

11. The system of claim 10, wherein the operating instructions comprise assembly instructions for assembling the wearable medical device.

12. The system of claim 1, wherein the augmented-reality enabled computing device further comprises a personal computing device used by at least one of the patient wearing the wearable medical device and a person other than the patient wearing the wearable medical device.

13. The system of claim 12, wherein the personal computing device comprises a wearable computing device configured to provide at least one of audio, video, and haptic feedback to the at least one of the patient and the person other than the patient via the display.

14. The system of claim 1, wherein the processor is further configured to:
establish a communication session with a remote communications device;
receive the contextual information relating to the wearable medical device from the remote communication device; and
augment the received video with the contextual information relating to the wearable medical device.

15. The system of claim 14, wherein the contextual information relating to the wearable medical device comprises troubleshooting information related to operation of the wearable medical device.

16. The system of claim 15, wherein the troubleshooting information comprises a set of instructions for a user of the wearable medical device to perform.

17. The system of claim 1, wherein the display is configured to display the video of the scene as a real-time or near-real time video of the scene.

18. The system of claim 1, wherein the context of the scene further comprises the patient viewing the patient wearing the wearable medical device in a mirror.

19. The system of claim 18, wherein the contextual information further comprises information related to a simulation of operation of the wearable medical device.

20. The system of claim 19, wherein the wearable medical device further comprises a wearable defibrillator and the contextual information further comprises a video simulation of the wearable defibrillator providing treatment to the patient.

21. The system of claim 1, wherein the context of the scene further comprises the patient wearing a prescribed wearable medical device prescribed by a physician to the patient and the contextual information comprises device information related to the prescribed wearable medical device.

22. The system of claim 1, wherein the context of the scene further comprises the patient viewing the body of the patient and the contextual information further comprises a visual overlay of at least one component of the wearable medical device as it would appear if being worn on the body of the patient.

23. The system of claim 1, wherein the video further comprises the patient wearing the wearable medical device.

24. The system of claim 23, wherein the context of the scene further comprises an environment of the patient wearing the wearable medical device.

25. The system of claim 1, wherein the contextual information further comprises ECG information for the patient determined by and received from the wearable medical device such that at least a portion of the ECG information is overlaid on the video of the scene and displayed on the display.

26. The system of claim 25, wherein the ECG information comprises heart rate information for the patient.

* * * * *